US005789594A

United States Patent [19]
Bringmann et al.

[11] Patent Number: 5,789,594
[45] Date of Patent: Aug. 4, 1998

[54] DIMERIC NAPHTHYLISOQUINOLINE ALKALOIDS AND SYNTHESIS METHODS THEREOF

[75] Inventors: Gerhard Bringmann; Sven Harmsen, both of Wurzburg, Germany; Michael R. Boyd, Ijamsville, Md.

[73] Assignee: The United States of America as represented by the Secretary of the Department of Health and Human Services, Washington, D.C.

[21] Appl. No.: 674,359

[22] Filed: Jul. 1, 1996

Related U.S. Application Data

[62] Division of Ser. No. 279,339, Jul. 22, 1994, Pat. No. 5,571,919.
[51] Int. Cl.$^6$ .................................................. C07D 401/10
[52] U.S. Cl. ........................... 546/140; 546/146; 546/147
[58] Field of Search .................................. 546/139, 140, 546/146, 147

[56] References Cited

U.S. PATENT DOCUMENTS

| | | | |
|---|---|---|---|
| 5,260,315 | 11/1993 | Bringmann et al. | 514/307 |
| 5,409,938 | 4/1995 | Boyd | 546/150 |

FOREIGN PATENT DOCUMENTS

| | | | |
|---|---|---|---|
| WO 92/18125 | 10/1992 | WIPO | 546/150 |

OTHER PUBLICATIONS

Benfield et al., "Studies of Fungal and Plant Laccases," *Phytochemistry*, 3, 79–88 (1964).
Bobbitt, et al., "Electrochemistry of Natural Products. III. A Stereoselective, Stereospecific Phenol Coupling Reaction," *J. Am. Chem. Soc.*, 93, 3551–3552 (1971).
Bringmann et al., "First total synthesis of korupensamines A and B," *Heterocycles*, 39(2), 503–508 (1994).
Boyd et al., "Anti–HIV Michellamines from *Ancistrocladus korupensis*," *J. Medicinal Chemistry*, 37(12), 1740–1745 (1994).
Bringmann, *The Alkaloids*, 29 (Brossi, ed.), Academic Press, New York, 1986, pp. 141–184.
Bringmann et al., "Isoquinolines and Naphthalenes from β–Polyketones: Model Reactions for an Extraordinary Alkaloid Biosynsthesis," *Angew. Chem. Int. Ed. Engl.*, 21(3), 200–201 (1982).
Bringmann et al., "Regioselective and Atropoisomeric–Selective Aryl Coupling to Give Naphthyl Isoquinoline Alkaloids: The First Total Synthesis of (–)–Ancistrocladine," *Angew. Chem. Int. Ed. Engl.*, 25(10), 913–915 (1986).
Bringmann et al., "The Absolute Configuration of Michellamine B, A 'Dimeric,' Anti–HIV–Active Naphthylisoquinoline Alkaloid," *Angew. Chem. Int. Ed. Engl.*, 32(8), 1190–1191 (1993).
Bringmann et al., "Chiral Economy with Respect to Rotational Isomerism: Rational Synthesis of Hamatine and (Optionally) Ancistrocladine from Joint Helical Precursors," *Heterocycles*, 28(1), 137–142 (1989).

Bringmann, "Biomimetische Synthesen beider Molekülhälften der Ancistrocladus–und der Triphyophyllum–Alkaloide aus gemeinsamen Vorstufen," *Liebigs Ann. Chem.*, 2126–2134 (1985).
Bringmann et al., "Atrop–diastereomer Separation by Racemate Resolution Techniques: N–Methyl–Dioncophylline A and its 7–Epimer from *Ancistrocladus abbreviatus*," *Phytochemistry*, 30(4), 1307–1310 (1991).
Bringmann et al., "Dioncopeltine A and Dioncolactone A: Alkaloids from *Triphyophyllum peltatum*," *Phytochemistry*, 30(5), 1691–1696 (1991).
Bringmann et al., "Dioncophylline B, A Naphtylisoquinoline Alkaloid with A New Coupling Type from *Triphyophyllum peltatum*," *Phytochemistry*, 30(11), 3845–3847 (1991).
Bringmann et al., "Ancistrobrevine B, The First Naphthylisoquinoline Alkaloid with a 5,8'–Coupling Site, and Related Compounds from *Ancistrocladus abbreviatus*," *Phytochemistry*, 31(11), 4011–4014 (1992).
Bringmann et al., "(±)–Dioncophyllacine A, A Naphthylisoquinoline Alkaloid with a 4–Methoxy Substituent from the Leaves of *Triphyophyllum peltatum*," *Phytochemistry*, 31(11), 4015–4108 (1992).
Bringmann et al., "Dioncophylline C from the Roots of the *Triphyophyllum peltatum*, the First 5,1'–Coupled Dioncophyllaceae Alkaloid," *Phytochemistry*, 31(11), 4019–4024 (1992).
Bringmann et al., "On the Biosynthesis of Acetogenic Tetrahydroisoquinoline Alkaloids: First In Vivo Feeding Experiments," *Planta Med.*, 57 (Suppl. 2), A98 (1991).
Bringmann et al., "Ancistrobrevine D: An Unusual Alkaloid from *Ancistrocladus abbreviatus*," *Planta Med.*, 58 (Suppl. 1), A703–704 (1992).
Bringmann et al., "A New Atropisomeric Dioncophylline A Derivative from *Triphyophyllum peltatum*," *Planta Med.*, 59 (Suppl.), A621–622 (1993).
Bringmann et al., "The Cultivation of Tropical Lianas of the Genus Ancistrocladus," *Planta Med.*, 59 (Suppl.), A623–624 (1993).
Bringmann et al., "On the Structure of the Dioncophyllaceae Alkaloids Dioncophylline A ('Triphyophylline') and 'O–Methyl–Triphyophylline,'" *Tetrahedron Letters*, 31(5), 639–642 (1990).

(List continued on next page.)

*Primary Examiner*—Zinna Northington Davis
*Attorney, Agent, or Firm*—Leydig, Voit & Mayer, Ltd.

[57] ABSTRACT

The present invention provides methods of preparing dimeric naphthylisoquinoline alkaloids by coupling together two monomeric naphthylisoquinoline alkaloids, each of which may be the same or different, and one, both, or neither of which may possess a C-8' to C-5 naphthalene/isoquinoline linkage, to form homodimers or heterodimers, including the antiviral michellamines. The present invention also provides new, medically useful homodimeric and heterodimeric naphthylisoquinoline compounds and derivatives thereof.

24 Claims, 18 Drawing Sheets

OTHER PUBLICATIONS

Bringmann et al., "First Total Synthesis of (−)-Dioncophylline A ('Triphyophylline') and of Selected Stereoisomers: Complete (Revised) Stereostructure," *Tetrahedron Letters*, 31(5), 643–646 (1990).

Bringmann et al., "Circular Dichroism of Michellamines: Independent Assignment of Axial Chirality by Calculated and Experimental CD Spectra," *Tetrahedron*, 50(26), 7807–7814 (1994).

Flaig et al., "Reaktionen Mit Oxydierenden Enzymen Aus Mikroorganismen," *Planta Med.*, 9, 123–139 (1961).

Fleischhauer et al., "Messung und Berechnung der CD-Spektren der Biaryl–Alkaloide Ancistrocladein und Dioncophyllein A," *Z. Naturforsch*, 48b, 140–148 (1993).

François et al., "Activity of Extracts and Naphthylisoquinoline Alkaloids from *Triphyophyllum peltatum*, *Ancistrocladus abbreviatus* and *A. barteri* against *Plasmodium falciparum* In Vitro." *Phytochemistry*, 35(6), 1461–1464 (1994).

Gulakowski et al., "A Semiautomated Multiparameter Approach for Anti–HIV Drug Screening," *J. Virological Methods*, 33, 87–100 (1991).

Harel et al., "Purification and Multiplicity of Catechol Oxidase from Apple Chloroplasts," *Phytochemistry*, 4, 783–790 (1965).

Holland, in *Organic Synthesis with Oxidative Enzymes*, Chapter 8, Miscellaneous Oxidative Bioconversions, "1. Oxidative Coupling of Phenols and the Formation of Quinones," VCH, Weinheim, 341–351, 380–381 (1992).

Laatsch, "Synthese von Biramentaceon, Mamegakinon und Rotundichinon," *Liebigs Ann. Chem.*, 1321–1347 (1980).

Nicholl, in *An Introduction to Genetic Engineering*, Cambridge Univ. Press, Cambridge, pp. 1–5 & 127–130 (1994).

Old et al., in *Principles of Gene Manipulation*, Blackwell Scientific Publishers, London, pp. 3–13 & 108–221 (1992).

Robb et al., On the Heterogeneity of the Tyrosinase of Broad Bean (Vicia Faba L.), *Pytochemistry*, 4, 731–740 (1965).

Saunders, *Peroxidase*, Butterworth, London, pp. 1–52 (1964).

Scott, "Oxidative Coupling of Phenolic Compounds," in *Quarterly Reviews* (London), 19, 1–35 (1965).

Sofer, *Introduction to Genetic Engineering*, Butterworth–Heinemann, Stoneham, MA, pp. 1–21 & 103–126 (1991).

Steinberg et al., in *Recombinant DNA Technology Concepts and Biomedical Applications*, Prentice Hall, Englewood Cliffs, NJ, pp. 81–124 & 150–162 (1993).

Supko et al., "Determination of Michellamine B in Biological Fluids by High–Performance Liquid Chromatograph with Fluorescence Detection," *Analytical Biochemistry*, 216, 52–60 (1994).

Thomas et al., "*Ancistrocladus korupensis* (Ancistrocladaceae): A New Species of Liana from Cameroon," *Novon*, 3(4), 494–498 (1993).

Vlietstra et al, "Trimethylacetic Formic Anhydride. Improved Preparation and Use As a Highly Efficient and Selective N–formylating Reagent," *J. Royal Netherlands Chemical Society*, 101, 460–462 (1982).

Whiting, in *Comprehnsive Organic Synthesis*, (Trost and Fleming, eds.), Peragamon Press, Oxford, pp. 659–703 (1991).

Bringmann et al., "Biomimetic oxidative dimerization of korupensamine A: Completion of the first total synthesis of michellamines A, B, and C," *Tetrahedron*, 50(32), 9643–9648 (1994).

Hoye et al., "Total synthesis of michellamines A–C: Important anti–HIV agents," *Tetrahedron Letters*, 35(47), 8747–8750 (1994).

Kelly et al., "Convergent total synthesis of the michellamines," *Tetrahedron Letters*, 35(41), 7621–7624 (1994).

Manfredi et al., "Novel alkaloids from the tropical plant *Ancistrocladus abbreviatus* inhibit cell killing by HIV–1 and HIV–2," *Journal of Medicinal Chemistry*, 34(12), 3402–3405 (1991).

["REDOX-NEUTRAL" PROCEDURES]

STRUCTURE 1

STRUCTURE 2

STRUCTURE 3

STRUCTURE 4

N-FORMYL-DIONCOPHYLLINE C

N-FORMYL-8-O-BENZYL-DIONCOPHYLLINE C

N-FORMYL-8-O-METHYL-DIONCOPHYLLINE C

N-FORMYL-8-O-PIVALOYL-DIONCOPHYLLINE C

N-FORMYL-8-O-ACETYL-DIONCOPHYLLINE C

MICHELLAMINE A
MICHELLAMINE B
MICHELLAMINE C

1

DIMERIC NAPHTHYLISOQUINOLINE ALKALOIDS AND SYNTHESIS METHODS THEREOF

"This is a divisional of application Ser. No. 08/279,339, filed on Jul. 22, 1994," now U.S. Pat. No. 5,571,919.

TECHNICAL FIELD OF THE INVENTION

The present invention relates to methods of preparing known and new dimeric naphthylisoquinoline alkaloids. The present invention also relates to new dimeric naphthylisoquinoline alkaloids and derivatives thereof.

BACKGROUND OF THE INVENTION

Novel compounds exhibiting impressive antiviral and/or antiparasitic properties have recently been described (Manfredi et al., *J. Med. Chem.*, 34, 3402–3405, 1991; Bringmann et al., *Angew. Chem. Int. Ed. Eng.*, 32, 1190–1191, 1993; Boyd et al., *J. Med. Chem.*, 37, 1740–1745, 1994; Boyd et al. U.S. Pat. No. 5,455,251 Bringmann et al., *Tetrahedron*, 50, 7807–7815, 1994a; Hallock et al., *J. Org. Chem.*, 59, 6349–6355, 1994b; Bringmann et al., *Heterocycles*, 39, 503–512, 1994; Bringmann et al., *Tetrahedron*, 50, 9643–9648, 1994c; Francois et al., *Phytochemistry*, 35, 1461–1464, 1994; Francois et al., U.S. Pat. No. 5,639,761; Boyd et al., U.S. Pat. No. 5,409,938; concurrently filed Bringmann et al., U.S. Pat. application Ser. No. 08/279,291. These compounds are members of a general class known as naphthylisoquinoline alkaloids (Bringmann, *The Alkaloids*, Vol. 29 (Brossi, ed.), Academic Press, New York, 1986, pp. 141–184), and can further be characterized based on their structure as either monomeric alkaloids (or "monomers") or dimeric alkaloids (or "dimers").

Monomeric alkaloids include korupensamines or related monomeric naphthylisoquinoline alkaloids and derivatives thereof, which typically possess a C-8' to C-5 naphthalene/isoquinoline linkage, and non-korupensamine or other monomeric naphthylisoquinoline alkaloids and derivatives thereof, which typically lack a C-8' to C-5 naphthalene/isoquinoline linkage.

Dimeric alkaloids include michellamines, which, based on their molecular structure, are comprised of two monomeric alkaloids coupled together (e.g., two monomeric or molecular "halves"). Furthermore, a given michellamine may be either "homodimeric" (comprised of two monomeric halves which are the same) or "heterodimeric" (comprised of two monomeric halves which are different).

Dimeric naphthylisoquinoline alkaloids, as exemplified by the michellamines, have highly desirable and eminently useful medicinal properties that for the most part are distinct from the properties of the monomeric naphthylisoquinoline alkaloids which comprise their molecular halves. For example, the michellamines, such as michellamine B (Boyd et al., U.S. Pat. No. 5,455,251; Boyd et al., 1994, supra), are highly effective inhibitors of the replication and resultant destructive effects of the human immunodeficiency virus (HIV) in human immune cells. The range of anti-HIV activity observed for these dimeric alkaloids is exceptionally broad, encompassing both the major viral types, HIV-1 and HIV-2, as well as diverse HIV strains, and can be observed in different host cells (Boyd et al., 1994, supra).

Moreover, the dimeric alkaloids would appear to comprise a novel antiviral drug class in that the mechanism of action of the michellamines is distinct from any mechanism previously described. Specifically, the mechanism involves at least two components: (1) an inhibition of the viral reverse transcriptase, and (2) an inhibition of the virus-cell and cell-cell fusion processes (McMahon et al., *Antimicrob. Agents Chemother.*, 39, 484–488 (1955). This suggests that the dimeric alkaloids may prove effective not only in the prevention of nascent viral infection, but also in the prevention of the replication and spread of the virus in vivo and in the prevention of syncytia formation which has been observed in vitro and which may mediate the depletion of T4 immune cells which occurs in vivo.

In addition to the medicinally desirable properties of the dimeric alkaloids, they are also quite attractive from a pharmacological and toxicological standpoint. In vivo doses of michellamine B that are non-toxic result in a level of the drug in the blood which is well in excess of its effective antiviral concentration (Supko et al., *Anal. Biochem.*, 216, 52–60, 1994; Supko et al., *Antimicrob. Agents Chemother.*, 39, 9–14 (1995).

In contrast, the monomeric naphthylisoquinoline alkaloids appear to be devoid of anti-HIV activity. However, the monomeric alkaloids instead have potent antiparasitic properties as exhibited by their bacteriocidal activity against strains of malaria. In this respect, it is interesting to speculate that a trace of this antiparasitic activity may be imparted to the alkaloid dimer by its constituent monomeric halves, as a few of the dimeric naphthylisoquinoline alkaloids (e.g., the michellamines), lso appear weakly antiparasitic (Boyd et al., U.S. Pat. No. 5,409,938; Francois et al., U.S. Pat. No. 5,455,251; Francois et al., supra).

Unfortunately, attempts by researchers to maximally exploit the potential of the dimeric alkaloids through development of antiviral and antiparasitic therapy and unprecedented uses for the alkaloids have been hindered by the lack of significant access to the dimeric alkaloids. To date, the only known natural source of the dimeric alkaloids is the rare tropical vine *Ancistrocladus korupensis* of Central Africa (Thomas and Gereau, *Novon*, 3, 494–498, 1993; Boyd et al., 1994, supra; Hallock et al., 1994, supra). Monomeric naphthylisoquinoline alkaloids do not spontaneously combine or couple together to form the dimeric alkaloids, and a method of converting (e.g., coupling) monomeric alkaloids or derivatives thereof to form a dimeric alkaloid or derivative has heretofore been unknown. Indeed, the naturally occurring michellamines A, B, and C (Boyd et al., 1994, supra) and frustratingly simple derivatives prepared directly therefrom (see, e.g., Boyd et al., U.S. Pat. No. 5,455,251 have been the only known dimeric naphthylisoquinoline alkaloids from anv source. Alternative dimeric alkaloids, if such be obtained, might present particularly advantageous medicinal properties, such as increased potency, increased host range, increased range of therapeutic action, and the like.

Accordingly, it is an object of the present invention to provide methods of synthesizing known and new dimeric alkaloids, including homodimeric and heterodimeric naphthylisoquinoline alkaloids.

Correspondingly, it is another object of the present invention to provide new dimeric alkaloids. Such compounds have particular use as therapeutic agents, for instance, as antiviral and antiparasitic agents, as exemplified by the michellamines (Bringmann et al., *Tetrahedron*, 50, 9643–9648, 1994; concurrently filed Bringmann et al., U.S. Pat. Application; Boyd et al., *J. Med. Chem.*, 37, 1740–1745, 1994; Francois et al., U.S. Pat. No. 5,639,761.

These and other objects and advantages of the present invention, as well as additional inventive features, will be apparent from the description of the invention provided herein.

BRIEF SUMMARY OF THE INVENTION

The present invention provides a method of preparing a compound which comprises (a) selecting first and second naphthylisoquinoline alkaloid monomers, which are either the same or different, (b) optionally introducing protective group(s) at desired site(s) in the monomers, (c) introducing activation group(s) at the desired coupling site(s) of the monomers if needed for coupling of the monomers, (d) coupling the first and second monomers to form a dimeric naphthylisoquinoline alkaloid, and (e) optionally removing the protective group(s) from the dimeric naphthylisoquinoline alkaloid.

The present invention also provides new dimeric naphthylisoquinoline alkaloids, as well as derivatives thereof.

DETAILED DESCRIPTION OF THE INVENTION

Figure 1:
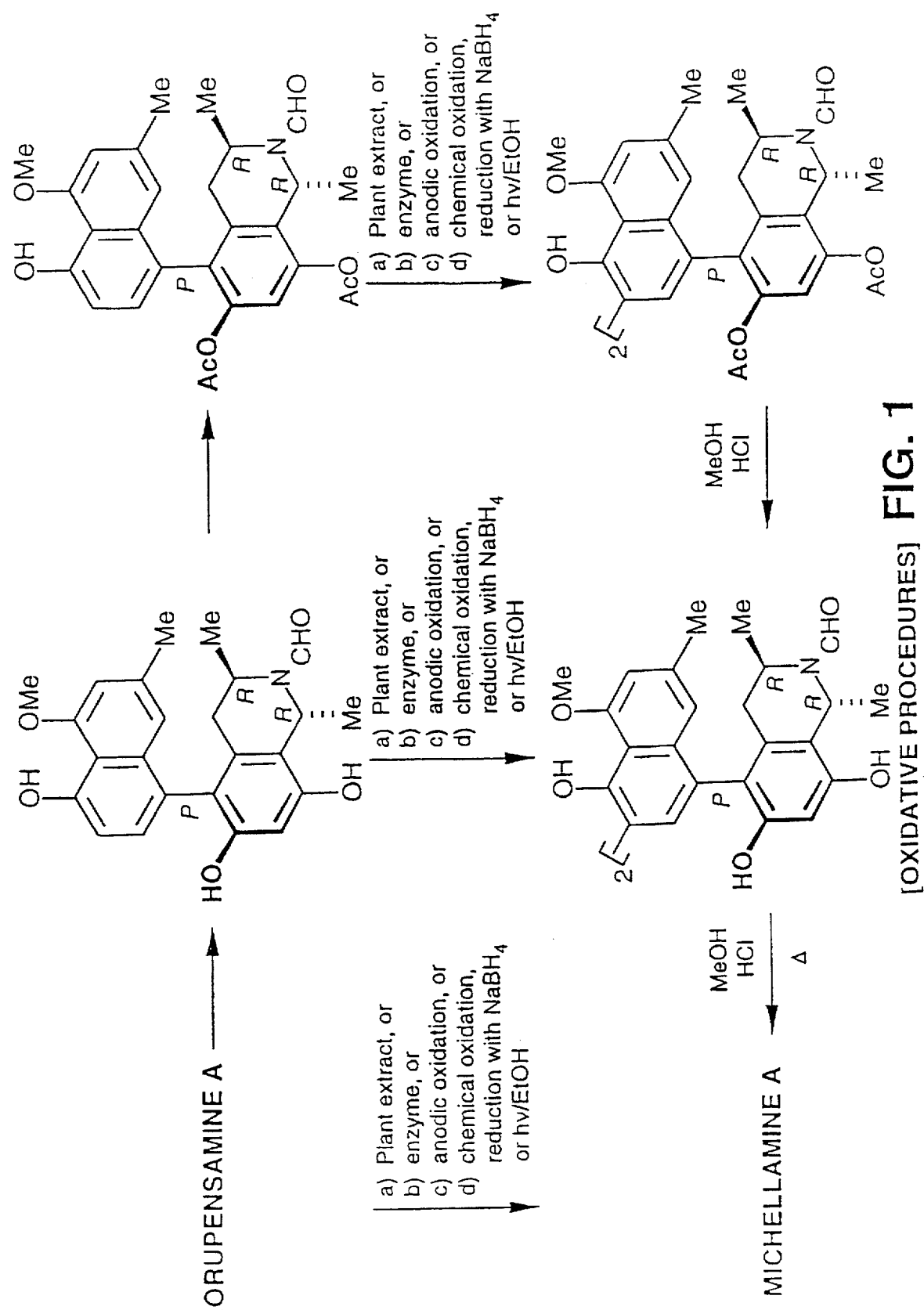
FIG. 1 illustrates some oxidative coupling procedures to make a medically useful dimeric naphthylisoquinoline alkaloid from a monomeric naphthylisoquinoline precursor.

The present invention provides methods of preparing both known and new dimeric naphthylisoquinoline alkaloids and derivatives thereof. The present invention also provides new dimeric naphthylisoquinoline alkaloids and derivatives thereof.

Definitions

For clarification of the chemical structures described herein, the following definitions apply.

By "korupensamine" or "related monomeric naphthylisoquinoline alkaloids" is meant a monomeric naphthylisoquinoline alkaloid possessing a C-8' to C-5 naphthalene/isoquinoline linkage.

By "non-korupensamine" or "other monomeric naphthylisoquinoline alkaloids" is meant a monomeric naphthylisoquinoline alkaloid which lacks a C-8' to C-5 naphthalene/isoquinoline linkage.

By naphthylisoquinoline homodimers is meant a dimeric alkaloid containing two monomeric naphthylisoquinoline halves, wherein each half is the same.

By naphthylisoquinoline heterodimers is meant a dimeric alkaloid containing two monomeric naphthylisoquinoline halves, wherein each half is different.

By $C_1$–$C_6$ alkyl is meant straight or branched-chain $C_1$–$C_6$ alkyl groups. Examples include, but are not limited to, methyl, ethyl, n-propyl, isopropyl, n-butyl, isobutyl, sec-butyl, tertiary-butyl, n-pentyl, isopentyl, and n-hexyl.

By aryl is meant an organic radical derived from an aromatic hydrocarbon. Examples of aryl groups include phenyl and o-, m-, and p-hydroxyphenyl.

By aliphatic is meant an organic radical derived from an open hydrocarbon chain. Examples of aliphatic radicals include alkanes, alkenes, and alkynes. Specific examples of aliphatic radicals which can be used in the present invention include, but are not limited to, $C_1$–$C_6$ alkyl radicals, straight or branched.

Structures

To make it easier to compare naphthylisoquinoline alkaloids of the present invention of different coupling types, contrary to IUPAC numbering conventions, and consistent with previous work by the inventors (Bringmann et al., *Phytochemistry*, 30, 3845–3847, 1991), the naphthalene portion of the alkaloids is hereinafter numbered in the same way. In other words, there is always attributed a 2-methyl-4,5-dioxy-substitution pattern to the naphthalene, independent from the site of the axis.

Medical Uses

The new dimeric naphthylisoquinoline alkaloids and derivatives thereof are expected to have at least those medicinal properties possessed by the previously known dimeric naphthylisoquinoline alkaloids (see, e.g., Boyd et al., U.S. Pat. No. 5,455,521; Boyd et al., 1994, supra). However, depending upon the particular disease and host to be treated, a compound of the present invention will be distinctly advantageous in a given situation.

Medically useful properties of the compounds of the present invention can be readily confirmed by one knowledgeable and skilled in the art by use of any of a variety of methods which have been published or otherwise disclosed elsewhere. For example, antiviral properties, particularly anti-HIV properties, can be confirmed as described in Boyd et al., *J. Med. Chem.*, 1994, supra, and Boyd et al., U.S. patent application Ser. No. 08/049,824. Also, for example, in vitro and in vivo antimalarial activity may be confirmed as described in Francois et al., *Phytochemistry*, 35, 1461–1464, 1994, Gulakowski et al., *J. Virol. Methods* 33, 87–100, 1991, Francois et al., U.S. patent application Ser. No. 08/195,547, and Boyd et al., U.S. Pat. No. 5,639,761.

Monomeric Naphthylisoquinoline Monomers Employed as Precursors in the Present Invention The concurrently filed Bringmann et al. U.S. patent application provides methods for preparing synthetic korupensamines and related C-8' to C-5 linked monomeric naphthylisoquinoline alkaloids, as well as nonkorupensamines and other monomeric naphthylisoquinoline alkaloids which lack a C-8' to C-5 naphthylisoquinoline linkage, and derivatives thereof, all of which may be employed as synthetic precursors in the present invention. Numerous other naturally occurring, monomeric naphthylisoquinoline alkaloids and semisynthetic derivatives thereof are also known (see, for example, Boyd et al., U.S. Pat. No. 5,639,761; Francois et al., U.S. patent application Ser. No. 08/195,547), and these likewise may be employed as synthetic precursors in the present invention.

A practical synthetic route of access to most of such naturally occurring compounds had not heretofore been available. However, the concurrently filed Bringmann et al. U.S. Patent Application discloses that such monomeric alkaloids can now be chemically synthesized and are likewise useful as synthetic precursors for the methods and compounds of the present invention. Examples of such precursor monomers which may now be obtained as synthetic, partially synthetic or natural products, include but are not limited to the monomers

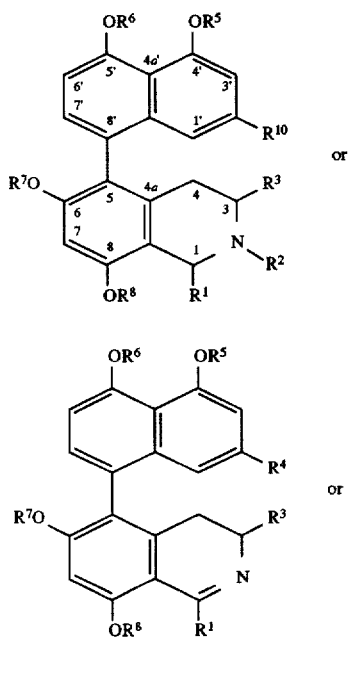

Figure 11:
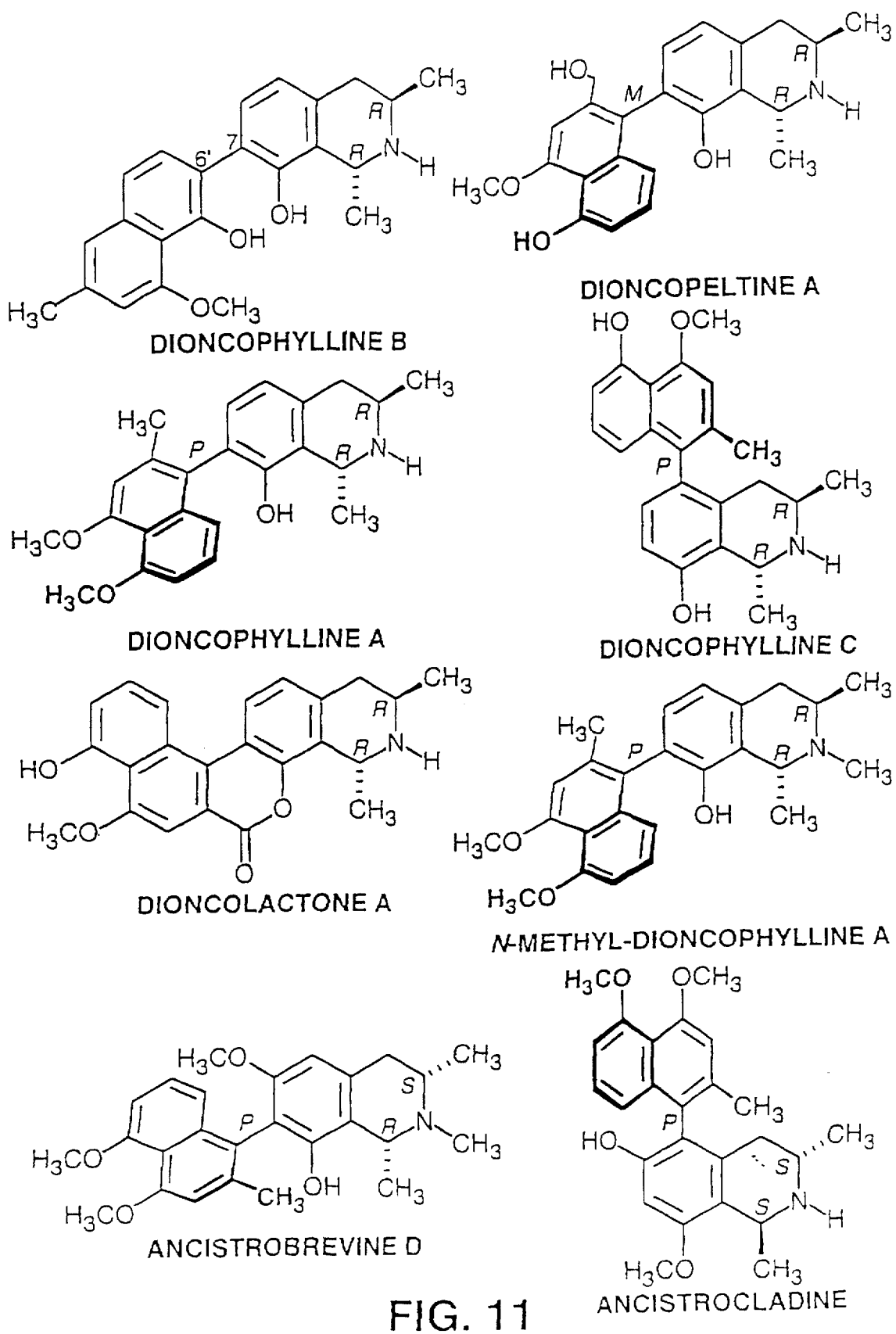
FIG. 11 illustrates the structures of various naphthylisoquinoline alkaloids.
Figure 11A:
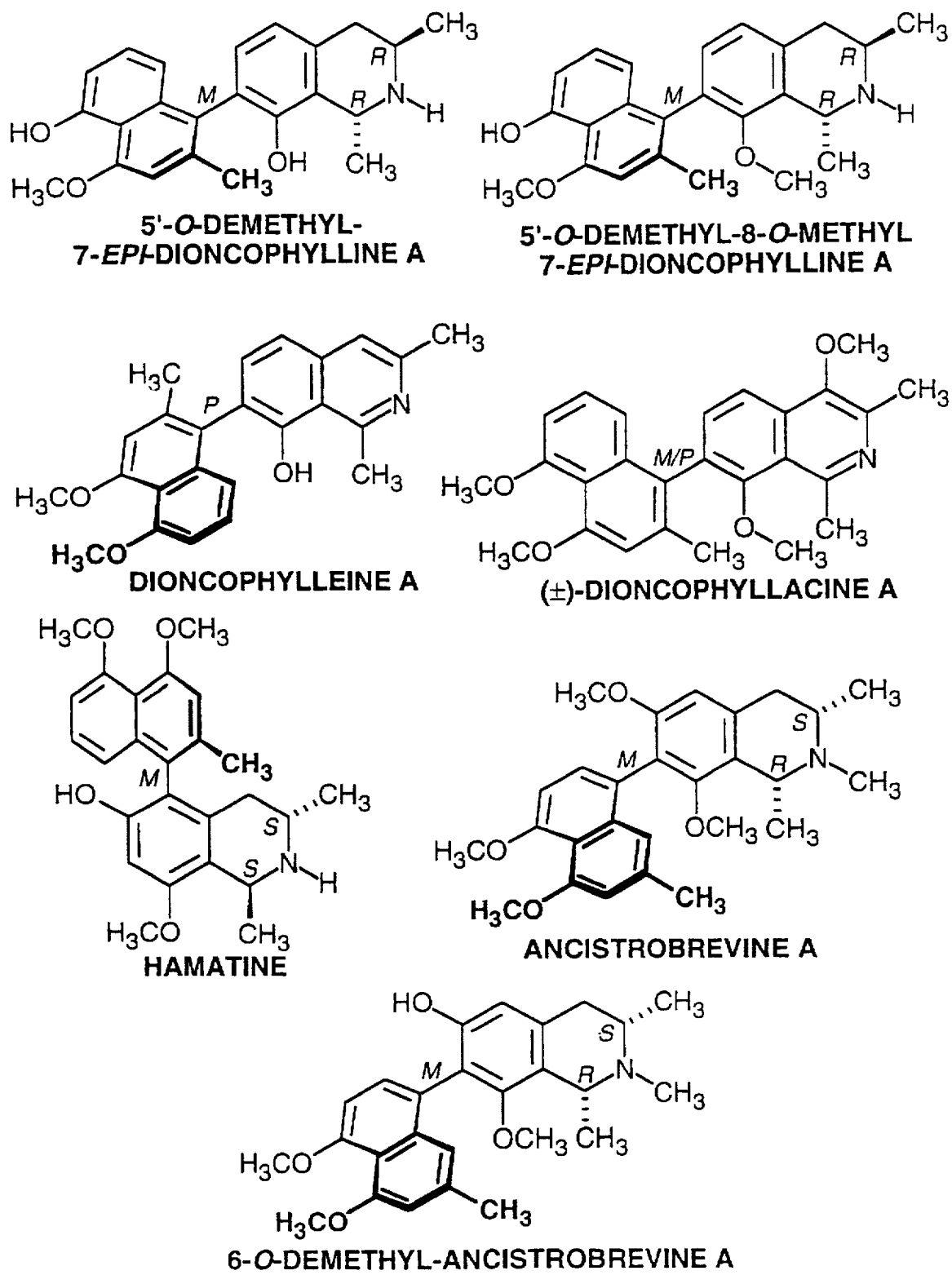
Figure 11B:
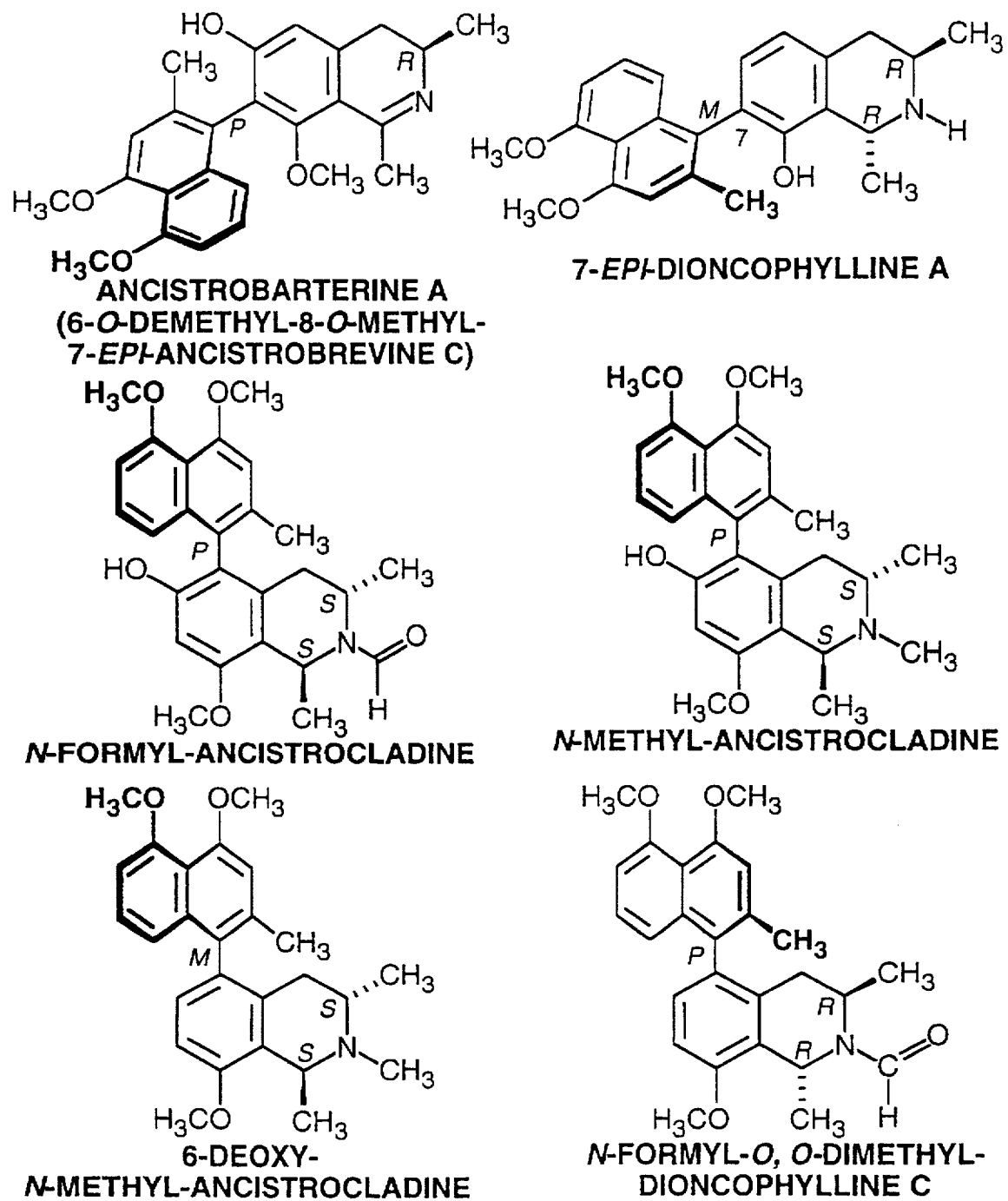
Figure 11C:
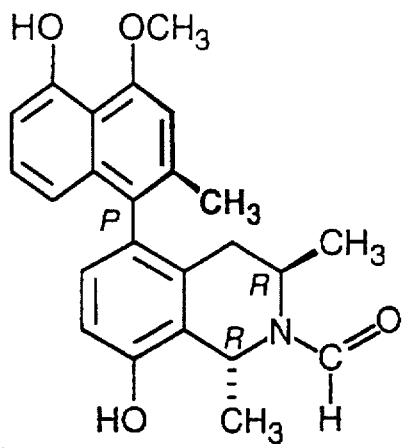
Figure 11C:
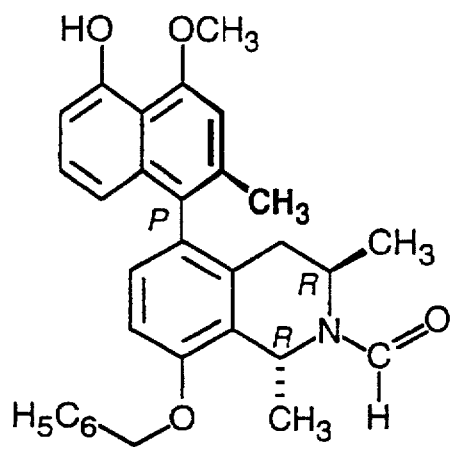
Figure 11C:
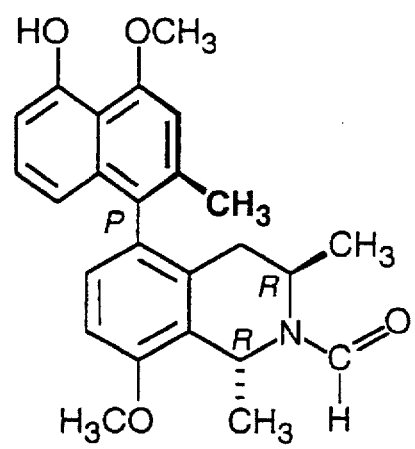
Figure 11C:
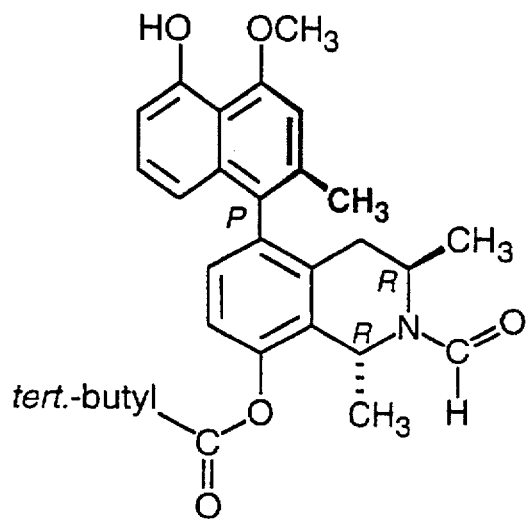
Figure 11C:
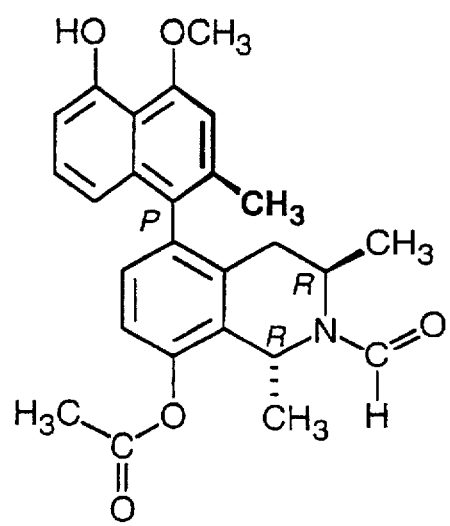
Figure 11D:
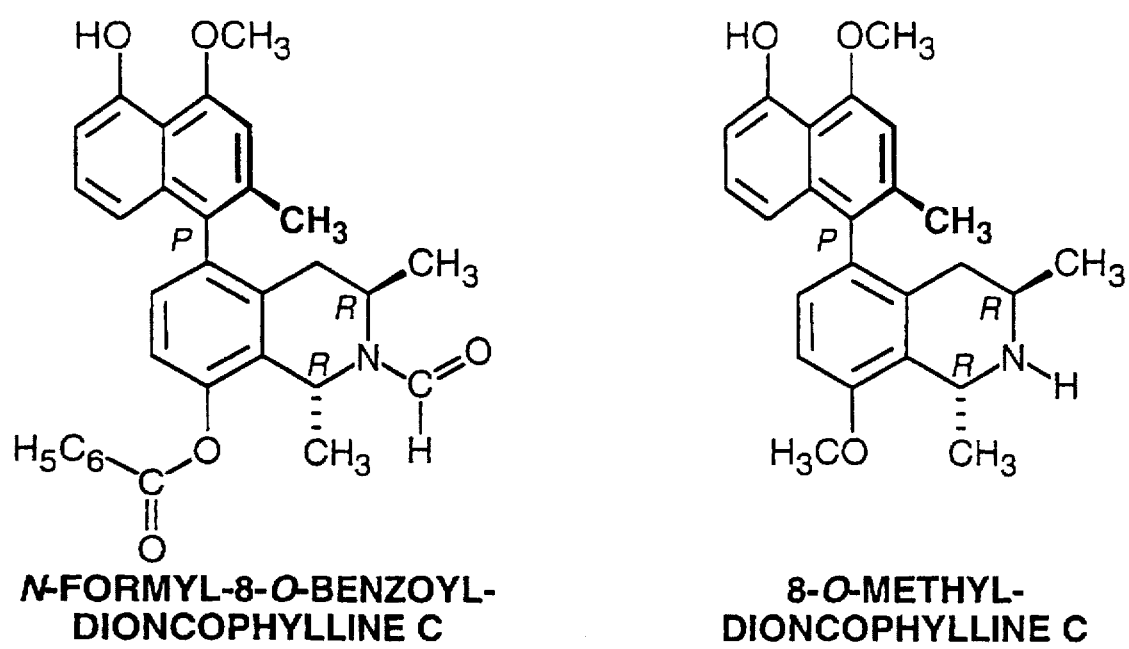

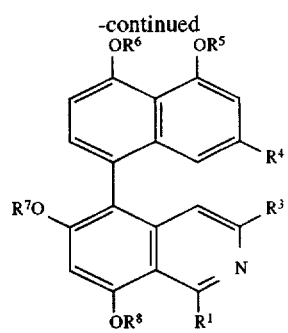

wherein $R^1$, $R^3$, $R_4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl, as well as monomers having the chemical formulae depicted in FIG. 11 (see also Table 1 which follows) and derivatives thereof.

TABLE 1

Literature references reporting the chemical structures of naphthylisoquinoline alkaloids.

| Compound Name | Reference Citation |
|---|---|
| Dioncophylline B | Bringmann et al., Phytochemistry, 30, 3845–3847, 1991 |
| Dioncopeltine A | Bringmann et al., Phytochemistry, 30, 1691–1696, 1991 |
| Dioncophylline A | Bringmann et al., Tetrahedron Lett., 31, 639–642, 1990; Bringmann et al., Tetrahedron Lett., 31, 643–646, 1990 |
| Dioncophylline C | Bringmann et al., Phytochemistry, 31, 4019–4024, 1992 |
| Dioncolactone A | Bringmann et al., Phytochemistry, 30, 1691–1696, 1991 |
| N-Methyl-dioncophylline A | Bringmann et al., Phytochemistry, 30, 1307–1310, 1991 |
| Ancistrobrevine D | Bringmann et al., Planta Med., 58 (suppl 1), 703–704, 1992 |
| Ancistrocladine | Bringmann, The Alkaloids, 29, 141–184, 1986 (and lit. cited therein) |
| N-Methyl-dioncophylline A (atropisomers) | Bringmann et al., Phytochemistry, 30, 1307–1310, 1991 |
| 5'-O-Demethyl-8-O-methyl-7-epi-dioncophylline A | Bringmann et al., Phytochemistry, 36, 1057–1061, 1994 |
| 5'-O-Demethyl-7-epi dioncophylline A | Bringmann et al., Planta Med., 59 (suppl), 621–622, 1993 |
| Dioncophylleine A | Fleischhauer et al., Z. Naturforsch, 48b, 140–148, 1993 |
| (±)-Dioncophyllacine A | Bringmann et al., Phytochemistry, 31, 4015–4018, 1992 |
| Hamatine | Bringmann et al., The Alkaloids, 29, 141–184, 1986; Bringmann et al., Angew Chem., 25, 913, 1986; Bringmann et al., Heterocycles, 28, 137, 1989 (and literature cited therein) |
| Ancistrobrevine A | Bringmann et al., Planta Med., 58 (suppl 1), 703–704, 1992 |
| 6-O-Demethyl-ancistrobrevine A | (unpublished) |
| Ancistrobarterine A (6-O-Demethyl-8-O-methyl-7-epi-ancistrobrevine C) | Bringmann et al., Planta Med., 59 (suppl), 623–624, 1993 |
| 7-epi-Dioncophylline A | Bringmann et al., Tetrahedron Lett., 31, 643–646, 1990 |
| N-Formyl-ancistrocladine | Bringmann et al., Phytochemistry, 31, 4019–4024, 1992 |
| N-Methyl-ancistrocladine | Bringmann et al., Phytochemistry, 31, 4019–4024, 1992 (and literature cited therein) |

TABLE 1-continued

Literature references reporting the chemical structures of naphthylisoquinoline alkaloids.

| Compound Name | Reference Citation |
| --- | --- |
| 6-Deoxy-N-methyl-ancistrocladine | Bringmann et al., Phytochemistry, 31, 4019–4024, 1992 |
| N-Formyl-O,O-dimethyl-dioncophylline C | Bringmann et al., Phytochemistry, 31, 4019–4024, 1992; |
| N-formyl-dioncophylline C | Bringmann et al., Phytochemistry, 31, 4019–4024, 1992 |
| N-Formyl-8-O-benzyl-dioncophylline C | François et al., U.S. Pat. No. 5,639,761 |
| N-Formyl-8-O-methyl-dioncophylline C | François et al., U.S. Pat. No. 5,639,761 |
| N-Formyl-8-O-pivaloyl-dioncophylline C | François et al., U.S. Pat. No. 5,639,761 |
| N-Formyl-8-O-acetyl-dioncophylline C | François et al., U.S. Pat. No. 5,639,761 |
| N-Formyl-8-O-benzoyl-dioncophylline C | François et al., U.S. Pat. No. 5,639,761 |
| 8-O-Methyl-dioncophylline C | François et al., U.S. Pat. No. 5,639,761 |

Synthesis of Dimeric Naphthylisoquinoline Alkaloids

The present invention provides a method of preparing a compound which comprises:

(a) selecting first and second naphthylisoquinoline alkaloid monomers, which are either the same or different, (b) optionally introducing protective group(s) at desired site(s) in the monomers, (c) introducing activation group(s) at the desired coupling site(s) of the monomers if needed for coupling of the monomers, (d) coupling the first and second monomers to form a dimeric naphthylisoquinoline alkaloid, and (e) optionally removing the protective group(s) from the dimeric naphthylisoquinoline alkaloid.

When the first and second monomers are the same, then their coupling results in a homodimeric naphthylisoquinoline alkaloid. Alternatively, when the first and second monomers are different, then their coupling results in a heterodimeric naphthylisoquinoline alkaloid.

The protective group(s) can be removed from the dimeric naphthylisoquinoline alkaloid by any suitable means, preferably by using methanolic HCl. Also, following synthesis, the dimeric naphthylisoquinoline alkaloid can be purified by any suitable means, preferably by HPLC, and especially on an amino-bonded or other phase column.

The present invention further comprises preferably introducing an OH substituent, or modification of an existing substituent to give an OH substituent, at the naphthalene ring position adjacent to the coupling site prior to the introduction of the protective group(s).

Any suitable protective and activation group(s) can be employed in the context of the present invention. The protective group(s) is/are preferably introduced by consecutive N-formylation then O-acetylation at all sites except the OH located immediately adjacent to the desired coupling site in each monomer. However, as described herein, the method of synthesis can be carried out wherein the protective group(s) is/are not introduced at all such sites.

The activation group will generally be nucleophilic on one monomer and electrophilic on the other monomer. Thus, the activation group for the first monomer is preferably selected from the group consisting of trialkylstannyl and boronic acid derivatives (nucleophilic group), while the activation group for the second monomer is preferably selected from the group of halogens, particularly bromine, and O-triflate leaving groups (electrophilic group). Introduction of the activation group may be accomplished by any suitable means, for example, by metallation followed by conversion to an activation group, such as trialkylstannyl or a boronic acid derivative.

The aforementioned process steps can be carried out by any suitable means. Thus, for example and as described further herein, the coupling can be effected by several means, including but not limited to: electrochemically; by transition metal catalysis, especially using Pd; by enzyme catalysis, particularly wherein the enzyme is selected from the group consisting of laccase, peroxidase, tyrosinase, and mixtures thereof, or wherein the enzyme is from the Ancistrocladus korupensis plant, either obtained by recombinant means, or purified directly from this source; oxidatively, especially wherein an oxidant, particularly $Ag_2O$, is used to give the corresponding binaphthyl, biaryl, or binaphthylidendione centered quateraryl derivative; reductively, especially wherein the coupling is done by introducing a halogen (in particular, bromine) at the coupling site(s), and then performing an Ullmann reaction; and by a "redox-neutral process", particularly wherein the activation group for the first monomer is trialkylstannyl or a boronic acid derivative, and the activation group for the second monomer is a halogen (especially bromine) or an O-triflate leaving group, particularly when the coupling is done by transition metal catalysis.

In a preferred method of the present invention, the protective group(s) is/are introduced by consecutive N-formylation then O-acetylation at all sites except the at the site of the OH located immediately adjacent to the desired coupling site in each monomer, and the coupling is effected using oxidants, preferably $Ag_2O$, to give the corresponding binaphthyl, biaryl, or biarylidendione centered quateraryl derivative, which is followed by photochemical or chemical reduction, to give the corresponding protected binaphthyl or biaryl derivative.

One skilled in the art will readily appreciate that certain chemical modifications can be incorporated as desired into the aforementioned synthetic method and/or can be used to modify the end product thereof to obtain a useful new synthetic dimeric naphthylisoquinoline alkaloid derivative. Such modified properties may include greater therapeutic potency against a particular disease or disease-causing organism, a broader spectrum of therapeutic activity against diverse diseases or disease-causing organisms, enhanced oral bioavailability, less toxicity in a particular host mammal, more advantageous pharmacokinetics and/or tissue distribution in a given host mammal, and the like. For example, by applying one or more well known chemical reactions to a given dimeric naphthylisoquinoline alkaloid, prepared according to the aforementioned method, a useful new derivative may be obtained wherein one or more phenolic hydroxyl group(s) may instead be replaced by an ester, sulfonate ester, or ether group; one or more methyl ether group(s) may instead be replaced by a phenolic hydroxyl group; one or more phenolic hydroxyl group(s) may instead be replaced by an aromatic hydrogen substituent; a secondary amine site may instead be replaced by an amide, sulfonamide, tertiary amine, or alkyl quaternary ammonium salt or corresponding Hoffmann elimination product thereof; a tertiary amine site may instead be replaced be a secondary amine; and one or more aromatic hydrogen substituent(s) may instead be replaced by a halogen, nitro, amino, hydroxyl, thiol, acyl, $C_1$–$C_6$ alkyl, or cyano substituent, and $CH_3$ may be replaced by H.

Alternatively, if a "modified" dimeric alkaloid is desired, such modifications may be contained within the monomeric alkaloids used to synthesize the dimer.

FIG. 1 schematically exemplifies some of the oxidative coupling approaches. Biosynthetic coupling may be achieved, for example, by catalysis using the whole *Ancistrocladus korupensis* plant (e.g., in the form of a homogenate) or subcellular fraction thereof, or other appropriate catalytic constituent(s), isolated or prepared therefrom. Such a constituent can be, for example, an enzyme which catalyzes the desired aforementioned coupling step.

An enzyme used for the aforementioned enzymatic coupling can be that isolated and purified directly from *Ancistrocladus korupensis* or, alternatively, a recombinant enzyme protein produced by well established genetic engineering techniques (see, e.g., Nicholl, in *An Introduction to Genetic Engineerin*, Cambridge University Press, Cambridge, 1994, pp. 1–5 & 127–130; Steinberg et al., in *Recombinant DNA Technology Concepts and Biomedical Applications*, Prentice Hall, Englewood Cliffs, NJ, 1993, pp. 81–124 & 150–162; Sofer, *Introduction to Genetic Engineering*, Butterworth-Heinemann, Stoneham, Mss, 1991, pp. 1–21 & 103–126; Old and Primrose in *Principles of Gene Manipulation*, Blackwell Scientific Publishers, London, 1992, pp. 1–13 & 108–221). For example, an *Ancistrocladus korupensis* gene or cDNA coding for such a coupling enzyme can be identified and subcloned. The gene or cDNA can then be delivered, using an appropriate expression vector, into an appropriate protein-synthesizing organism (e.g., *E. coli*, S. cerevisiae, insect cells, or mammalian cells) wherein the gene, under the control of an endogenous or exogenous promoter, can be appropriately transcribed and translated. Such expression vectors (including, but not limited to, phage, cosmid, viral, and plasmid vectors) are known to those skilled in the art, as are reagents and techniques appropriate for gene transfer (e.g., transfection, electroporation, transduction, microinjection transformation, etc.). Subsequently, the desired recombinantly produced protein can be isolated and purified using standard techniques known in the art for the purification of proteins (e.g., chromatography, centrifugation, differential solubility, isoelectric focusing, etc.), and used for the aforementioned enzymatic coupling reaction.

Alternatively, the desired native enzymatic protein for the aforementioned coupling reaction can be isolated, purified from Ancistrocladus korupensis by conventional (i.e., non-recombinant) methods, and sequenced by conventional techniques. The sequence can then be used to synthesize the corresponding DNA, which may then be subcloned into an appropriate expression vector, and delivered into a protein-producing cell for en mass recombinant production of the desired coupling enzyme.

In both cases, the DNA or cDNA encoding the coupling enzyme may code for either the entirety or a portion of the coupling protein. Where the DNA or cDNA does not comprise the entire coding sequence, the DNA or cDNA may be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as least some of the translational control sequences (i.e., the translation initiation codon) will be provided by the vector. In the case of a translational gene fusion, a chimeric protein will be produced.

Enzymes from sources other than *Ancistrocladus korupensis* can be used instead to catalyze the aforementioned coupling reaction. Examples of such enzymes include but are not limited to laccases (e.g., Benfield et al., *Phytochemistry*, 3, 79–88, 1964; Flaig et al., *Planta Med.*, 9, 123–139, 1961), peroxidases (e.g., Saunders, *Peroxidase*, Butterworth, London, 1964, pp. 1–52; Scott, *Ouart. Rev.* (London), 19, 1–35, 1965), and tyrosinases (e.g., Robb, *Phytochemistry*, 4, 731–740, 1965; Harel, *Phytochemistry*, 4, 783–790, 1965). This approach is further illustrated, for example, in recent reviews (e.g., Holland, *Organic Synthesis with Oxidative Enzymes*, (VCH Weinheim, ed.), 1992, p. 341; Whiting, in *Comprehensive Organic Synthesis* (Trost and Fleming, eds.), Pergamon Press, Oxford, 1991, VII, p. 659).

Figure 2:
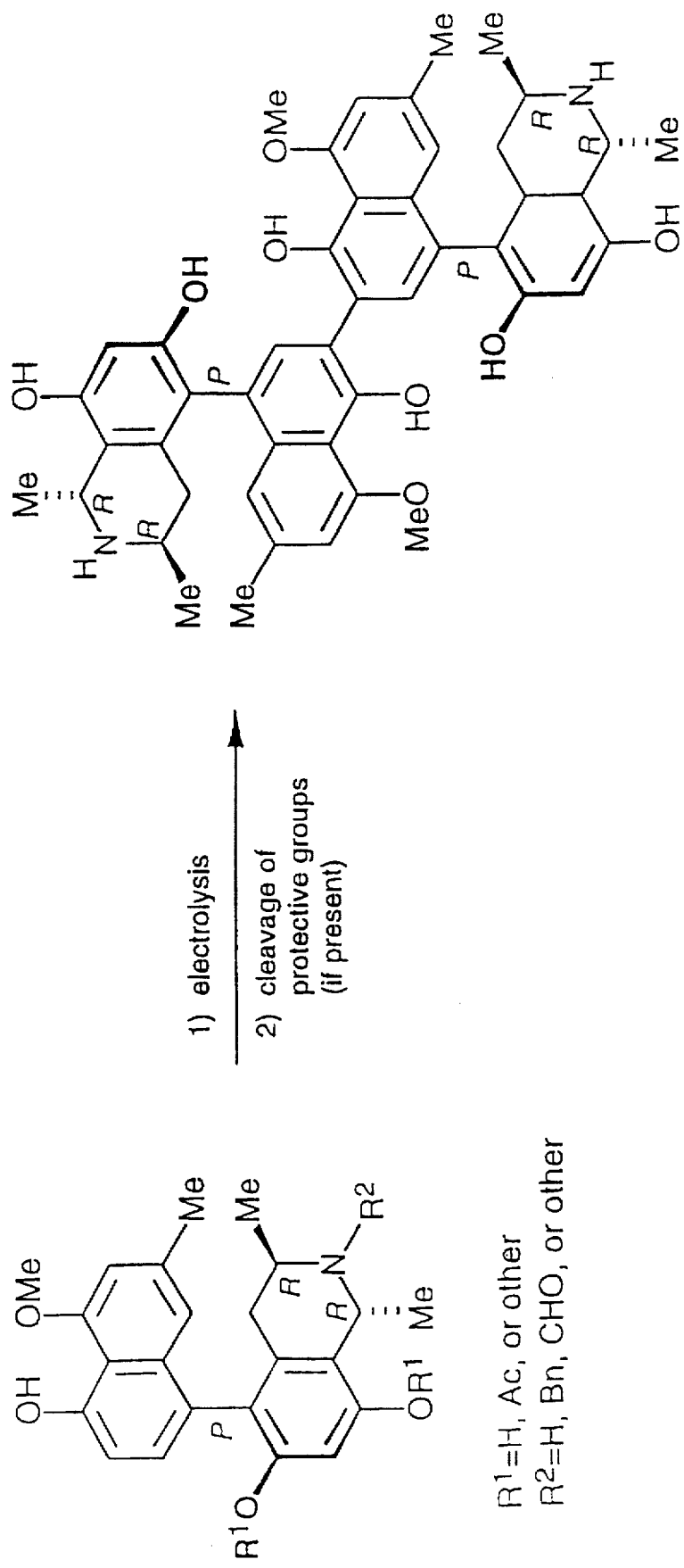
FIG. 2 illustrates an electrochemical coupling procedure to make a medically useful dimeric naphthylisoquinoline alkaloid from a monomeric naphthylisoquinoline precursor.

One skilled in the art will also appreciate that the aforementioned essential coupling step can be also performed electrochemically. For example, a solution of N-formyl-6, 8-O-bisacetyl korupensamine A (2) may be prepared and subjected to electrolysis, generally according to the procedure of Bobbitt et al. (*J. Am. Chem. Soc.*, 93, 3551–3552, 1971), to give the corresponding dimer. This is further illustrated schematically in FIG. 2.

Figure 3:
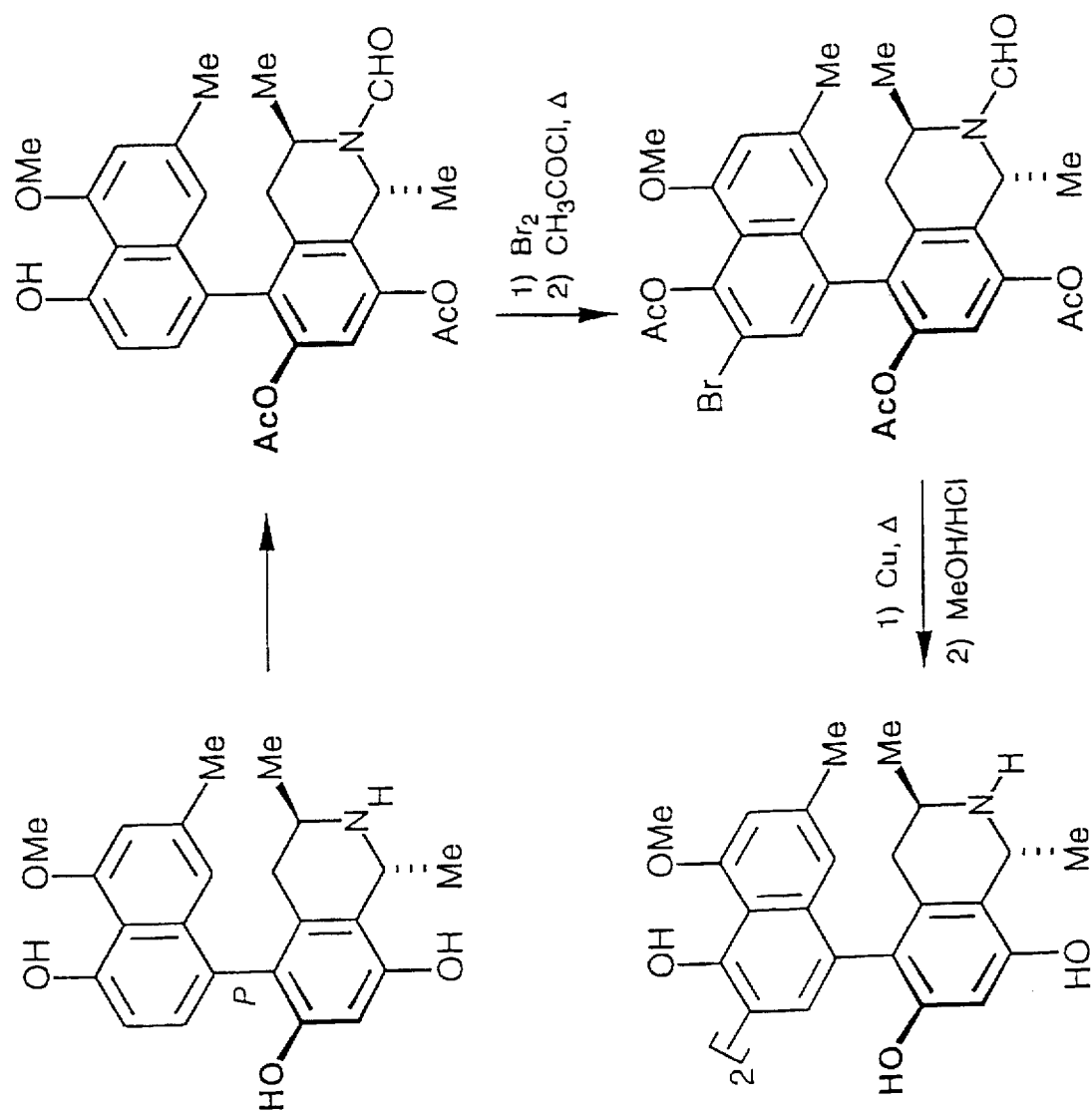
FIG. 3 illustrates a chemical reductive coupling procedure to make a medically useful dimeric naphthylisoquinoline alkaloid from a monomeric naphthylisoquinoline precursor.

The skilled artisan will further appreciate that the aforementioned essential coupling step can be likewise performed chemically by reduction, for example by reductive dimerization. In this instance, as is typical of non-oxidative coupling procedures in general, an activation of the coupling position(s) is required. For example, a halogen such as bromine may be introduced at the desired coupling position, followed by an Ullmann reaction to join the desired monomeric "halves". Thus, the N-formyl-6,8-O-bisacetyl korupensamine A can be selectively monobrominated by reaction with $Br_2$, then subsequently protected at the site of the last remaining free OH group by acetylation under more rigorous reaction conditions. The reductive coupling step by the Ullmann reaction is performed in a suitable solvent by heating (e.g., to 200° C.) with activated copper powder. Usual workup and cleavage of the protective groups provides michellamine A. This is further exemplified schematically in FIG. 3. Alternatively, korupensamine A may be benzylated at N-2, O-6, and O-8 to give N-benzyl-6,8-di-O-benzylkorupensamine which is protected with the MOM-group at O-5 and regioselectively halogenated by ortho-directed lithiation and treatment with an appropriate halogen source.

Figure 4:
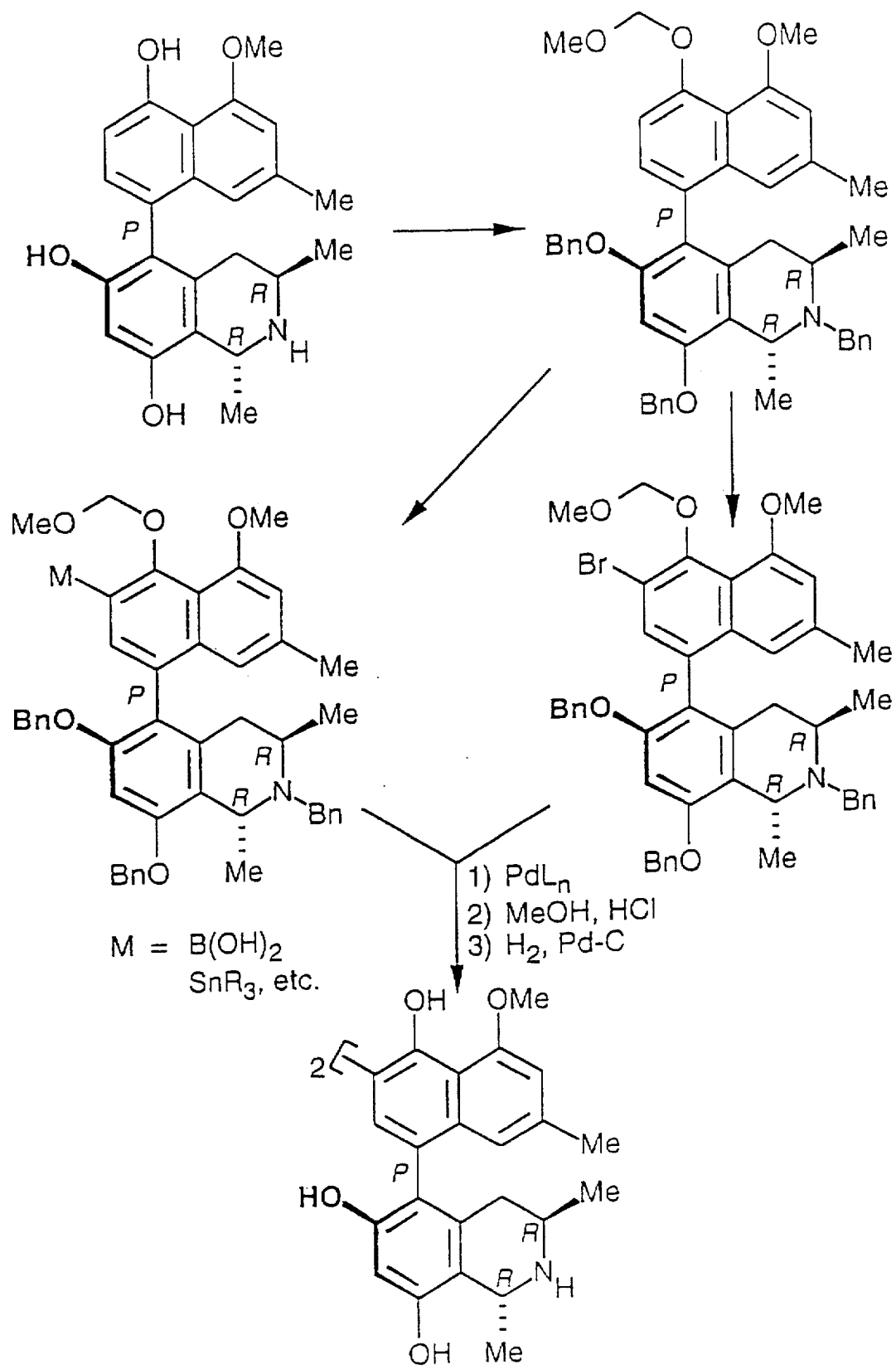
FIG. 4 illustrates a "redox-neutral" chemical coupling procedure to make a medically useful dimeric naphthylisoquinoline alkaloid from a monomeric naphthylisoquinoline precursor. Due to the electrophilic/nucleophilic character of the two appropriately prepared monomeric naphthylisoquinoline alkaloids, this procedure is particularly suited for the directed cross-coupling of two different monomeric alkaloids to give heterodimeric naphthylisoquinoline compounds.

The aforementioned essential coupling step can also be efficiently accomplished by a "redox-neutral" coupling process. Thus, the N-benzyl-6,8-O-benzylkorupensamine A is metallated and converted into an appropriate activation group such as the corresponding trialkylstannyl or boronic acid derivative, which is then reacted with the corresponding bromo-substituted derivative with Pd-catalysis. Ultimate cleavage of the protective group (if desired) gives the corresponding dimei.c target molecule. This is further exemplified in FIG. 4. This "redox-neutral" procedure is highly efficient in the preparation of heterodimeric naphthylisoquinoline alkaloids, because the electrophilic and nucleophilic reaction partners may be derived from different monomeric naphthylisoquinoline alkaloids appropriately prepared by the corresponding protective group strategy.

The aforementioned essential coupling step can also be very efficiently and effectively accomplished chemically by an oxidative dimerization process. Consequently, the present invention is directed yet more specifically to methods of preparing diverse medically useful dimeric naphthylisoquinoline alkaloids, particularly by employing an oxidative coupling step to join the desired monomeric halves.

Figure 12:
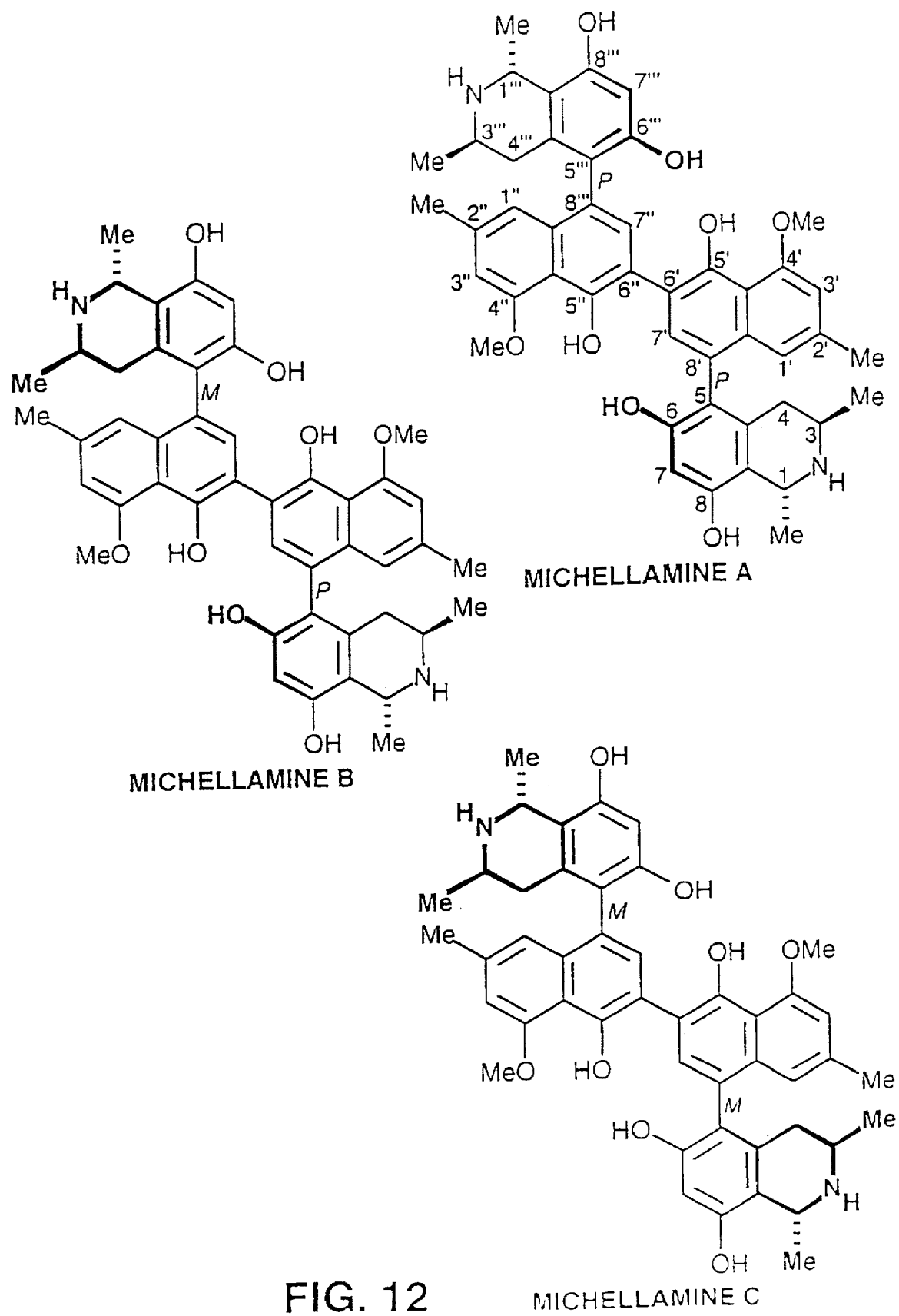
FIG. 12 illustrates the structures of various michellaminese

Dimeric Naphthylisoquinoline Alkaloids containing a C-8' to C-5 Naphthalene/Isoquinoline Linkage Within Both Molecular Halves and Derivatives Thereof The michellamines are characterized by the presence of no less than 6 free phenolic hydroxy groups and 2 secondary amino functions and, stereochemically, by the existence of 4 stereocenters and 3 axes, one of which is configuratively unstable, and the other two of which are stereogenic due to restricted rotation. As illustrated in FIG. 12, michellamines A and C in particular are $C_2$symmetric homodimers consisting of two constitutionally and stereochemically identical halves, whereas michellamine B is a heterodimer consisting of two atropodiastereomeric parts.

The present invention provides a novel method of chemical synthesis whereby one can build up the dimeric naphthylisoquinoline alkaloid framework through coupling of first and second naphthylisoquinoline monomers which represent the corresponding monomeric "halves" of the dimer. The present invention encompasses the aforementioned method wherein the first and second monomers are the same or different, especially wherein the monomers possess a C-8' to C-5 naphthalene/isoquinoline linkage, and preferably wherein the monomers are compounds of the formula

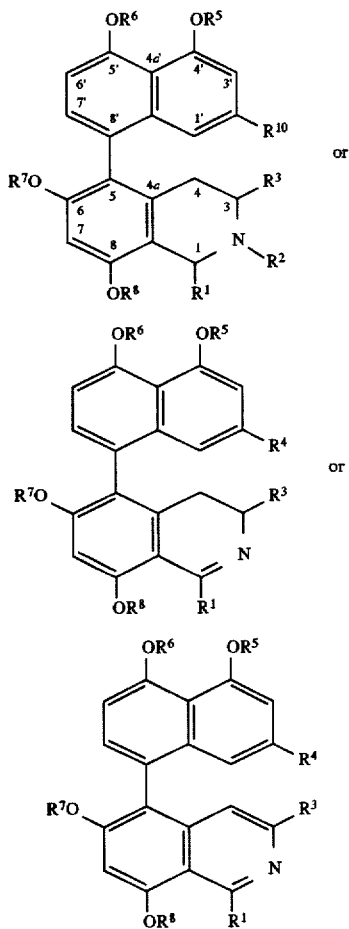

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

Figure 5:
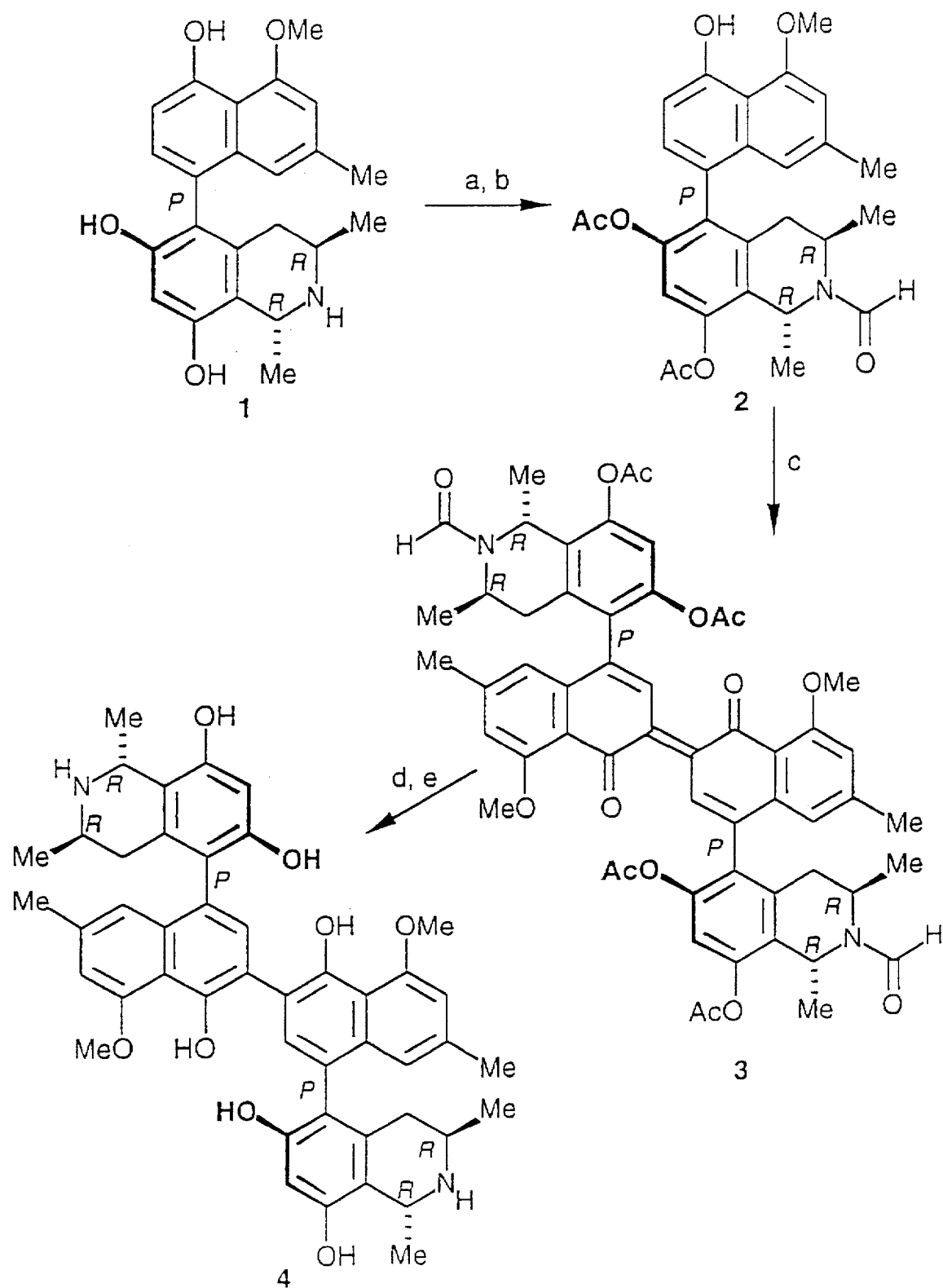
FIG. 5 illustrates a method for preparation of michellamine A through the oxidative dimerization of korupensamine A (1) via its derivative 2. Reaction conditions: (a) $(CH_3)_3CO_2CHO$, $CH_2Cl_2$ 20° C.; (b) $CH_3COCl$, $Et_3N$, cat. DMAP, $CH_2Cl_2$, 92% from 1; (c) $Ag_2O$, 0.2% $Et_3N$ in $CHCl_3$, 73%; (d) $NaBH_4$, iPrOH, 25° C.; (e) MeOH/HCl, reflux, 67% from 3.

The synthetic scheme for michellamine A provides a specific illustration of the method of synthesis of a homodimeric alkaloid containing a C-8' to C-5 naphthalene/isoquinoline linkage, and is set forth in FIG. 5. From the structure of the given precursor 1 (i.e., korupensamine A), with its phenolic oxygen functions and the secondary amino group, undesired by-products might be expected for the oxidation step. Also, such polar compounds are more difficult to handle. Consequently, it is necessary to guarantee selectivity for the coupling reaction already on the level of a specific protection of all these functionalities except for 5'–OH, i.e., the oxygen function next to the required coupling site. Thus, consecutive N-formylation with pivalic formic anhydride (Vlietstra et al., *J.R. Neth. Chem. Soc.*, 101, 460–462, 1982) and subsequent treatment with acetyl chloride clearly allows differentiation of the "free" hydroxy functions at C-6 and C-8 from the chelated one at C-5', specifically giving the partially protected monophenolic derivative 2 in most satisfactory (e.g., 90%) yields.

With the key monomeric precursor 2 thus in hand, the crucial dimerization step can be achieved with optimum yields (e.g., 90–95%) when using conditions elaborated in Laatsch et al., *Liebigs Ann. Chem.*, 1321–1347, 1980, for the dimerization of related naphthol precursors. Thus, treatment of 2 with $Ag_2O$ in $CHCl_3$ in the presence of 0.2% triethylamine leads directly to the formation of corresponding binaphthylidendione 3, without the necessity of stopping the reaction on the level of an intermediate binaphthol. Still, the easy detection of the violet-colored diquinone 3 and its satisfying stability makes this compound a convenient intermediate that can be fully characterized. Subsequent cautious reduction of 3, e.g., with sodium borohydride or with methanol/hv, gives the corresponding substituted binaphthol, with the central biaryl axis then in the correct position and oxidation level. No complications by the formation of atropodiastereomeric products needs to be taken into consideration, due to the low isomerization barrier at the central axis. Subsequent cleavage of all the 6 protective groups in the multifold derivatized michellamine A is then performed in a single step, by treatment with methanolic HCl, to give the pure michellamine A (4) in good yields (e.g., 60% from 3) with cleanup as necessary or desired by HPLC on an amino-bonded phase column. The synthetic product can be shown to be identical to the corresponding natural product by a comparison of its physicochemical, spectral, and biological properties to an authentic sample of the natural product (Manfredi et al., 1991, supra; Boyd et al., 1994, supra). Additional details can be found in Example 1.

It is also noteworthy that the oxidative phenolic coupling reaction can be, in certain favorable instances, successfully accomplished (albeit generally with somewhat less efficiency) using less fully protected or even unprotected monomers. For example, N-formyl-korupensamine A (i.e., not having further O-protective groups) can be coupled and deprotected in accordance with the immediately aforementioned procedure to give michellamine A. However, this synthetic route typically results in much poorer yields than in the aforementioned procedure which includes the use of O-protective groups. Likewise, it can be anticipated that coupling can be accomplished with completely unprotected monomers (e.g., lacking also the N-protective functionality), however, with still expected worse yields than when any protection/deprotection strategy is employed.

Certain naturally occurring michellamine compounds, and derivatives prepared directly therefrom, are described in U.S. Pat. No. 5,455,251, and published patent applications WO 92/18125 and WO 94/24108. As part of the present invention, those michellamine compounds and derivatives can now be obtained by chemical synthesis, which may be partially or entirely independent of the aforementioned natural products, by use of the aforementioned method and by employing synthetic C-8' to C-5 linked korupensamines or derivatives prepared according to the method of the concurrently filed Bringmann et al. U.S. Patent Application. Likewise, unprecedented new synthetic dimers, in which both of the monomeric halves retain a C-8' to C-5 naphthalene/isoquinoline linkage, yet which otherwise differ (e.g., in the chirality of stereocenter(s) or biaryl axis (axes), in the nature of the isoquinoline group(s), or in the position of coupling points of the monomeric halves) from the michellamines known to occur in nature, can be prepared.

Figure 6:
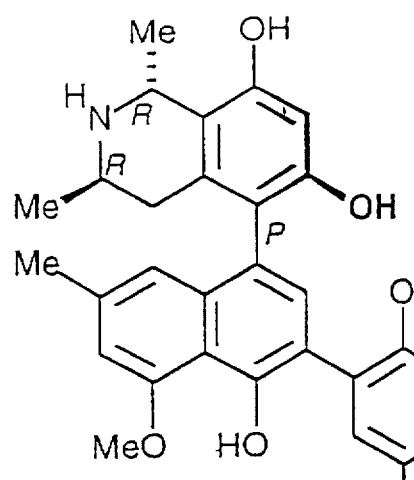
FIG. 6 illustrates some representative examples of variations in structures of the dimeric naphthylisoquinoline alkaloids which can be obtained according to the methods of the present invention.
Figure 6:
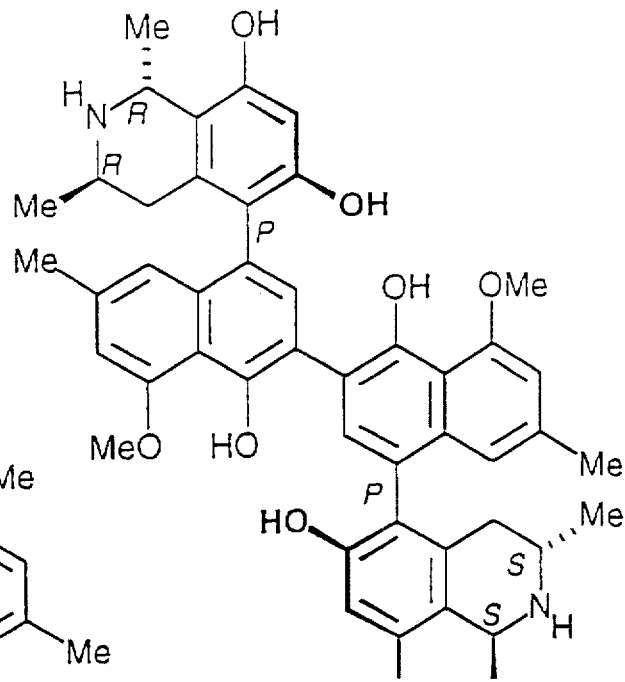
Figure 6:
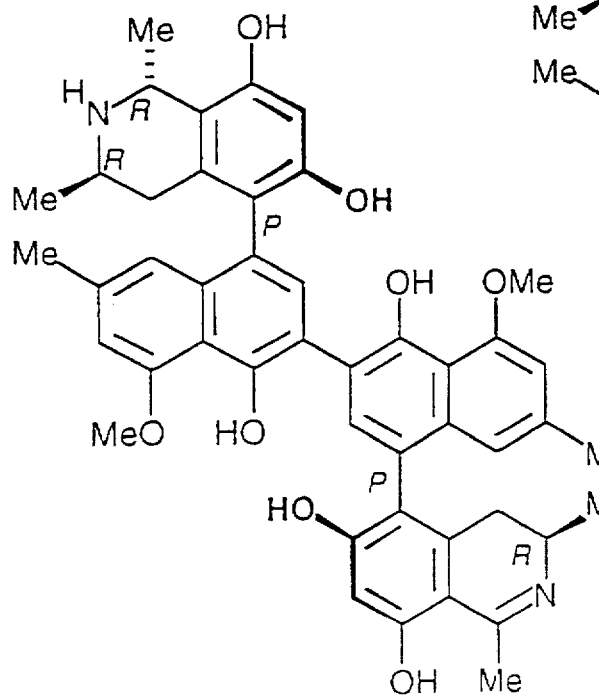
Figure 6:
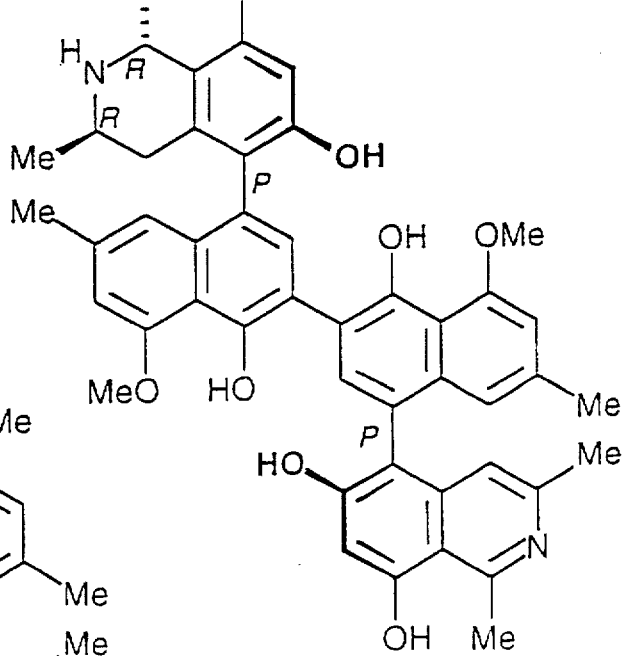

Some specific examples of variations in structure of such dimeric naphthylisoquinoline alkaloids which can be prepared according to the present invention are provided in FIG. 6. Structure 1 is michellamine A; structure 2 exemplifies a corresponding dimer wherein one of the korupensamine halves is instead replaced by a monomer which retains a C-8' to C-5 naphthalene/isoquinoline linkage and has different stereochemistry at C-1 and/or C-3; structure 3 exemplifies a corresponding compound having one or both tetrahydroquinolines replaced by a dihydroisoquinoline; structure 4 exemplifies a corresponding compound having one or both tetrahydroisoquinoline(s) or dihydroisoquinoline(s) replaced by a fully aromatic isoquinoline. In addition to, or instead of, variations such as exemplified by these structures, there may be other variations, such as different configurations (e.g., M or P) about the axis of coupling, different coupling positions, and/or different substituents on the naphthalene and/or isoquinoline portion(s) of the molecule.

Accordingly, the present invention provides new compounds, particularly dimeric michellamines and other dimeric naphthylisoquinoline compounds and derivatives thereof which possess a C-8' to C-5 naphthalene/isoquinoline linkage within both molecular halves. More specifically, the present invention provides a dimeric naphthylisoquinoline compound, or derivative thereof, wherein each monomeric half is the same or different and is comprised of a monomeric naphthylisoquinoline alkaloid which possesses a C-8' to C-5 naphthalene/isoquinoline linkage.

Thus, the present invention provides a dimeric naphthylisoquinoline alkaloid comprised of coupled first and second naphthylisoquinoline monomers which are the same or different, wherein said first and second monomers are compounds of the formula

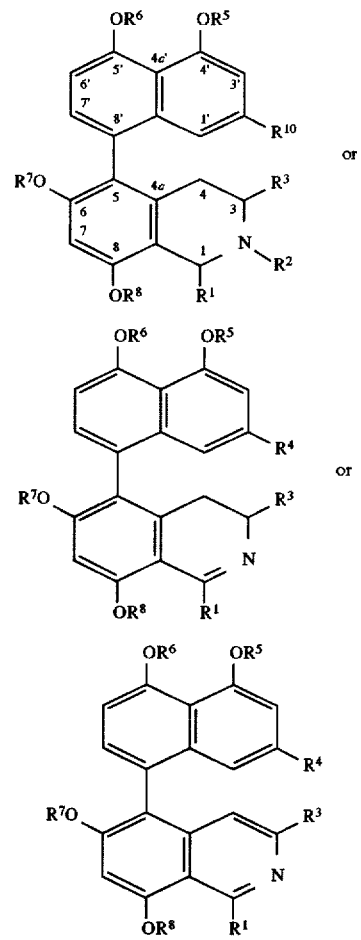

wherein $R^1$, $R^3$, $R^4$, and $R^{10}$ may be the same or different and each may be H or $C_1-C_6$ alkyl, $R^2$, $R^5$, $R^6$, $R^7$, and $R^8$ may be the same or different and each may be H, $C_1-C_6$ alkyl, $R^9CH_2-$, $R^9CO-$, or $R^9SO_2-$, $R^9$ may be H, $C_1-C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1-C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine, with the proviso that $R^{10}$ is not methyl in both first and second monomers when $R^1$ and $R^3$ are methyl in both first and second monomers.

Dimeric Naphthylisoquinoline Alkaloids Lacking a C-8' to C-5 Naphthalene/Isoquinoline Linkage Within One or Both of the Monomeric Halves The aforementioned method of coupling korupensamines and related naphthylisoquinoline alkaloids to provide dimers (e.g., michellamines) can be further applied, extended, and adapted as appropriate to provide yet other heretofore unknown dimeric naphthylisoquinoline alkaloids. For example, one or both of the monomeric halves comprising such a dimer may contain a non-korupensamine which lacks a C-8' to C-5 naphthalene/isoquinoline linkage that typifies the korupensamines and "korupensamine-like" monomers. Thus, for instance, one can select a monomeric compound of Table 1 to couple with the same or a different monomeric compound of Table 1, or with a korupensamine or related C-8' to C-5 linked monomer, to provide a new homodimeric or heterodimeric naphthylisoquinoline alkaloid. The choice of monomers for coupling into dimers is exemplified by, but is not limited to, the korupensamines and derivatives thereof and the compounds and derivatives thereof of Table 1. Still yet other suitable precursor monomers may be found in nature. In this respect, the concurrently filed Bringmann et al. U.S. Patent Application provides methods of synthesis of other diverse monomers having different linkages and/or chirality which may serve likewise as precursors for coupling into novel dimers.

Thus, the present invention encompasses a method of preparing a homodimeric or heterodimeric naphthylisoquinoline alkaloid which lacks a C-8' to C-5 naphthalene/isoquinoline linkage within one or both of the monomeric halves. The present inventive method of preparing a dimeric naphthylisoquinoline alkaloid through coupling of first and second monomers which form the corresponding monomeric halves of the dimeric naphthylisoquinoline alkaloid may also be employed wherein the first and second monomers are the same or different, and one or both of the first and second monomers lack a C-8' to C-5 naphthalene/isoquinoline linkage.

Suitable such monomers which lack a C-8' to C-5 naphthalene/isoquinoline linkage include the group consisting of dioncophylline B, dioncopeltine A, dioncophylline A, dioncophylline C, dioncolactone A, Nmethyl-dioncophylline A, ancistrobrevine D, ancistrocladine, 5'-O-demethyl-8-O-methyl-7-epidioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1-C_6$ alkyl, or cyano substituent, $CH_3$ may instead be H, and the tetrahydroisoquinoline may instead be a dihydroisoquinoline or a fully aromatic isoquinoline.

When only one of the monomers lacks a C-8' to C-5 naphthalene/isoquinoline linkage and the other monomer possesses a C-8' to C-5 naphthalene/isoquinoline linkage, the monomer possessing a C-8' to C-5 naphthalene/isoquinoline linkage can be a compound of the formula

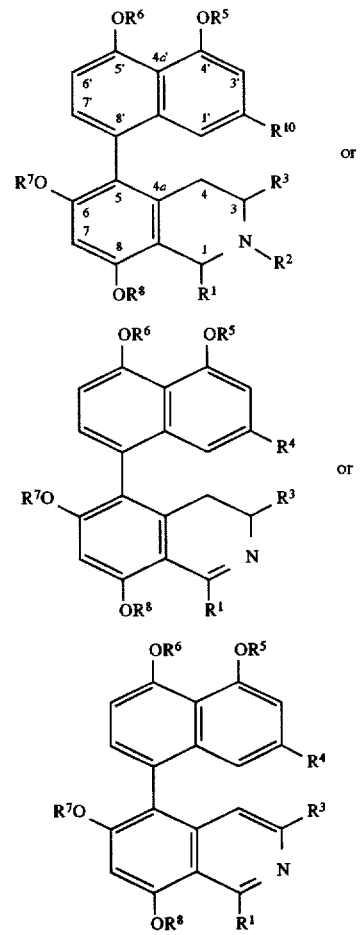

wherein $R^{1'}$, $R^3$, $R^4$ and $R^{10}$ may be the same or different and each may be H or $C_1-C_6$ alkyl, $R^2$, $R^5$, $R^6$, $R^7$, and $R^8$ may be the same or different and each may be H, $C_1-C_6$ alkyl, $R^9CH_2-$, $R^9CO-$, or $R^9SO_2-$, $R^9$ may be H, $C_1-C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1-C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

Figure 7:
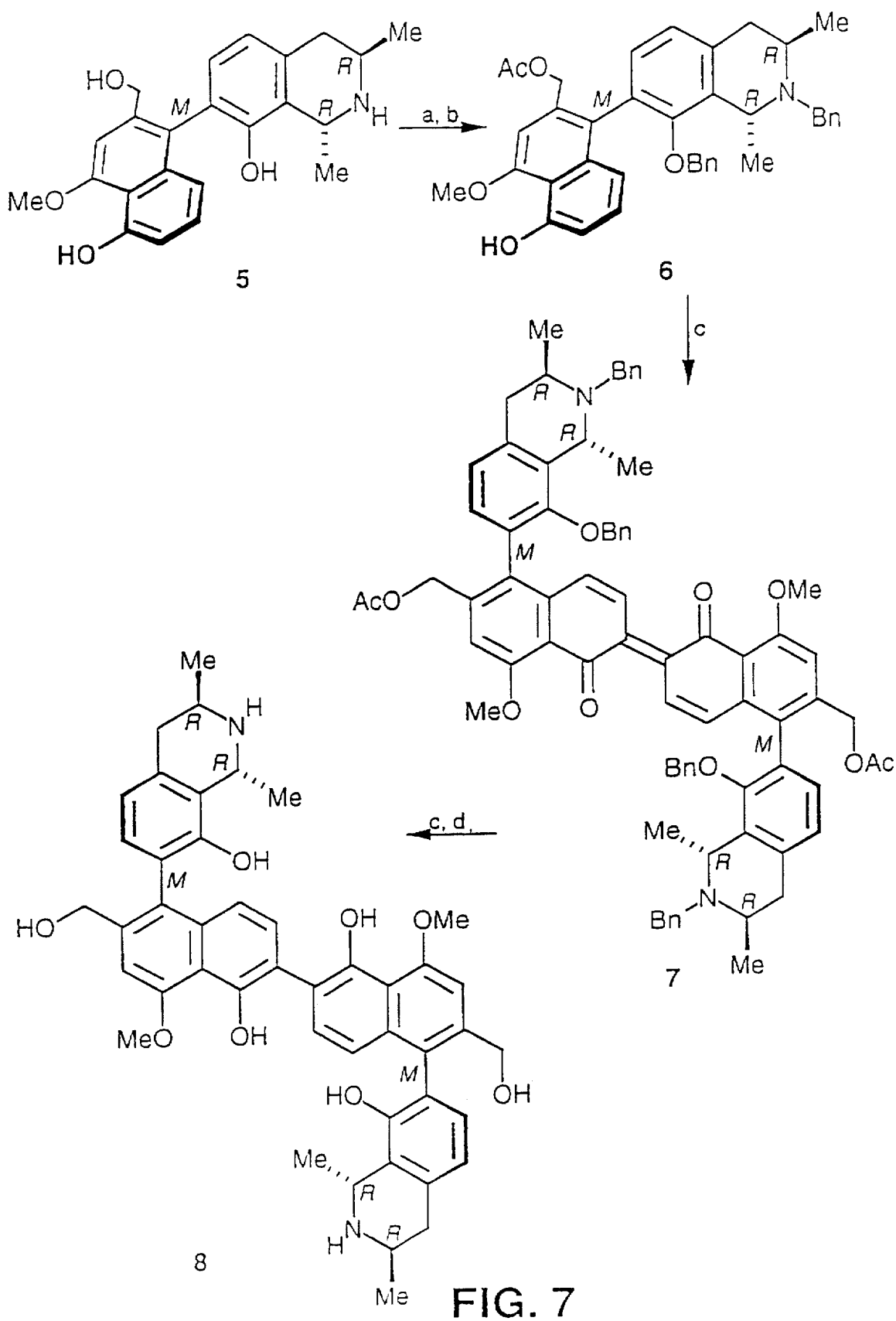
FIG. 7 illustrates a method for preparation of a representative new dimeric naphthylisoquinoline alkaloid. Shown specifically is a homodimer comprised of two monomeric dioncopeltine A "halves". Each of the halves lacks a C-8' to C-5 naphthalene/isoquinoline linkage.

As a yet more specific example, the aforementioned method can be applied to the synthesis of a heretofore unknown dimeric naphthylisoquinoline alkaloid 8 comprised of two dioncopeltine A "halves", as illustrated in FIG. 7. As before in the case of korupensamine A, the naturally occurring alkaloid dioncopeltine A (5), as isolated from Triphyophyllum peltatum (Bringmann et al., Phytochemistry, 30, 1691–1696, 1991), can subsequently be protected by N-formylation with pivalic formic anhydride and subsequent O-acetylation with AcCl, thus protecting all the nucleophilic functionalities except for the OH group at C-5' to give 6. Subsequent cautious oxidation with $Ag_2O$ gives the dimeric compound 7, which may be deprotected as in the aforementioned synthesis of michellamine A to give the novel dimer 8. Further details are provided in Example 2.

Figure 8:
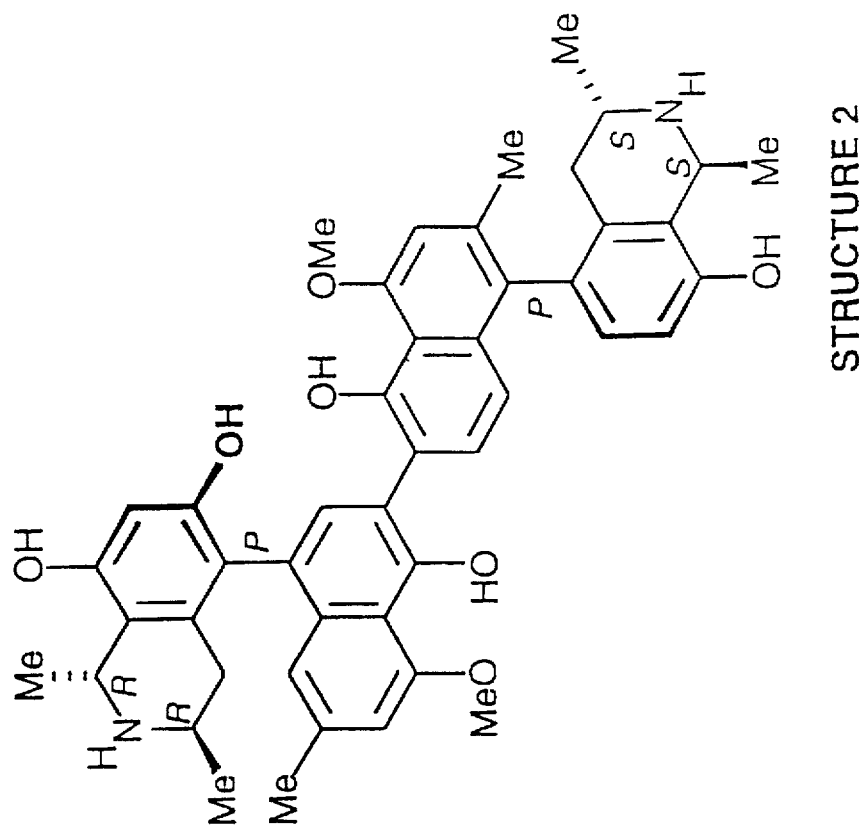
FIG. 8 illustrates some other representative examples of variations in the structures of the dimeric naphthylisoquinoline alkaloids which can be obtained according to the methods of the present invention.
Figure 8:
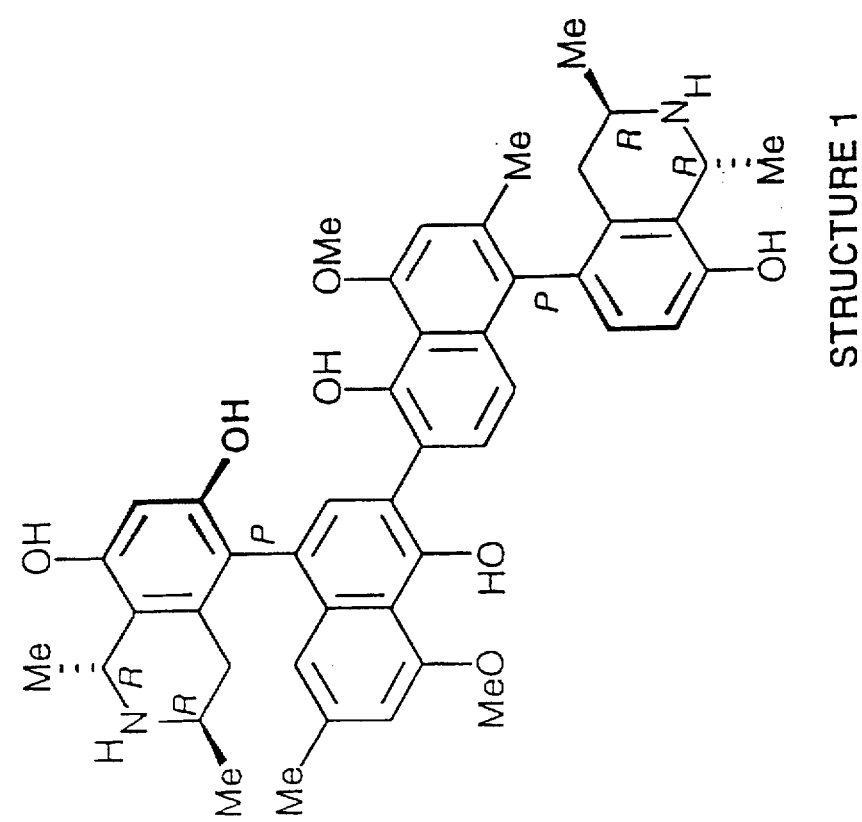
Figure 8A:
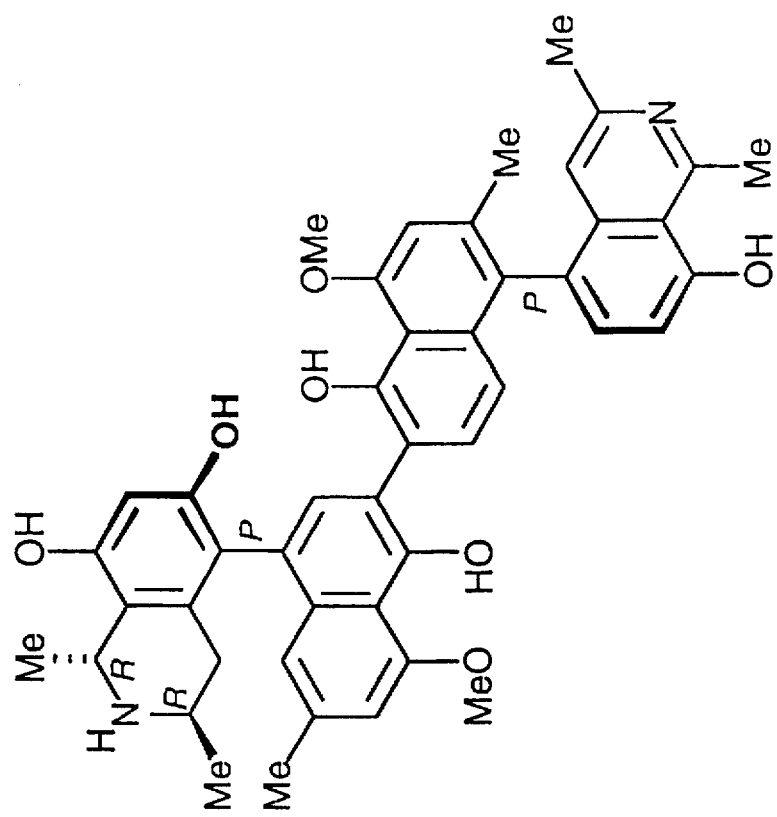
Figure 8A:
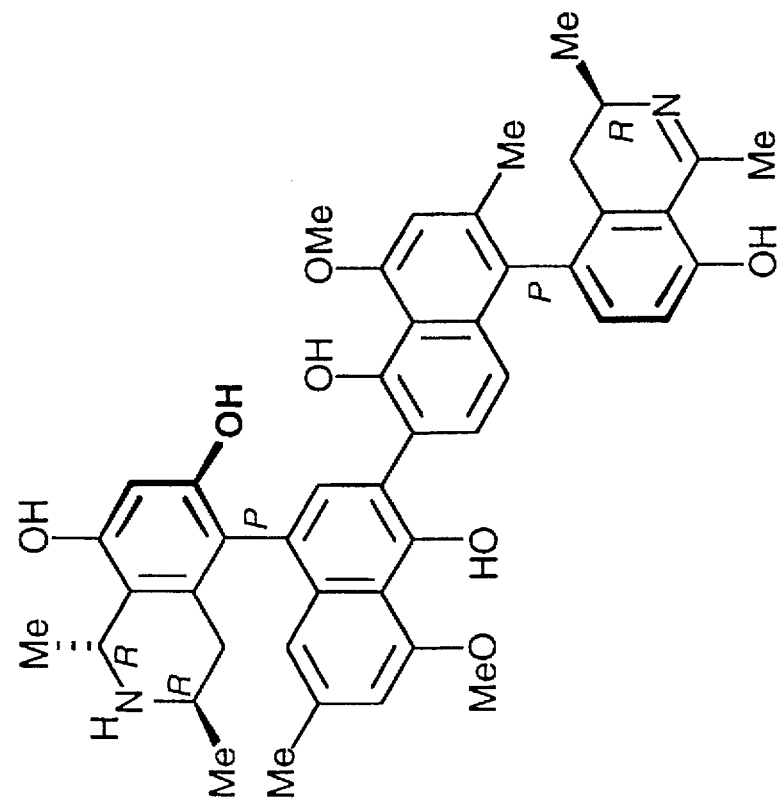

FIG. 8 illustrates some other selected examples of variations in the dimeric naphthylisoquinoline alkaloids which can be obtained according to the methods of the present invention. Structure 1 is a heterodimer comprised of one korupensamine monomeric half (which possesses a C-8' to C-5 naphthalene/isoquinoline linkage) coupled to a dioncophylline C monomeric half (which lacks a C-8' to C-5 naphthalene/isoquinoline linkage); structure 2 exemplifies a corresponding dimer wherein one or both of the monomeric halves instead has (have) a different configuration at C-1 and/or C-3; structure 3 exemplifies a corresponding compound having one or both tetrahydroisoquinolines replaced by a dihydroisoquinoline; structure 4 exemplifies a corresponding compound having one or both tetrahydroisoquinoline(s) or dihydroisoquinoline(s) replaced by a fully aromatic isoquinoline. In addition to, or instead of, variations such as exemplified by these structures, there may be other variations, such as different configurations (e.g., M or P) about the axis of coupling, different coupling positions, and/or different substituents on the naphthalene and/or isoquinoline portion(s) of the molecule.

Figure 9:
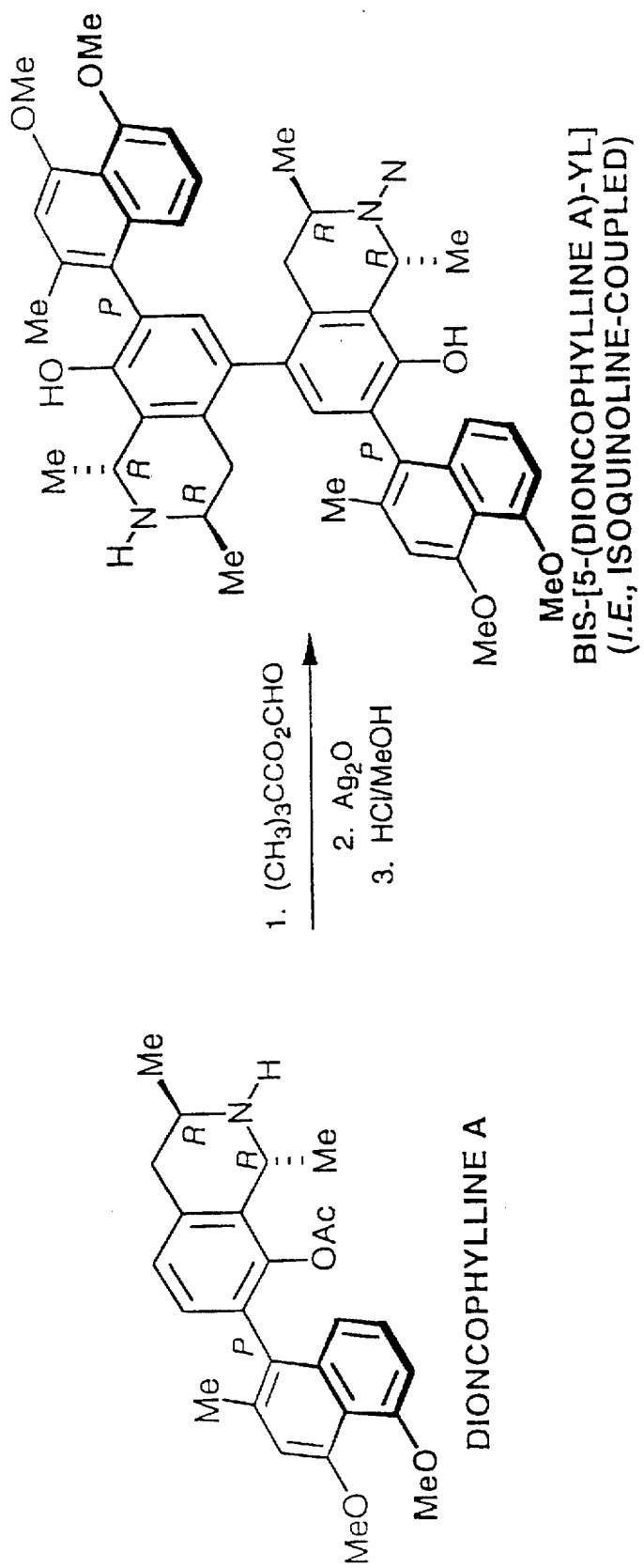
FIG. 9 illustrates a synthetic scheme for the preparation of isoquinoline-coupled versus naphthalene-coupled dimers of dioncophylline A.
Figure 9A:
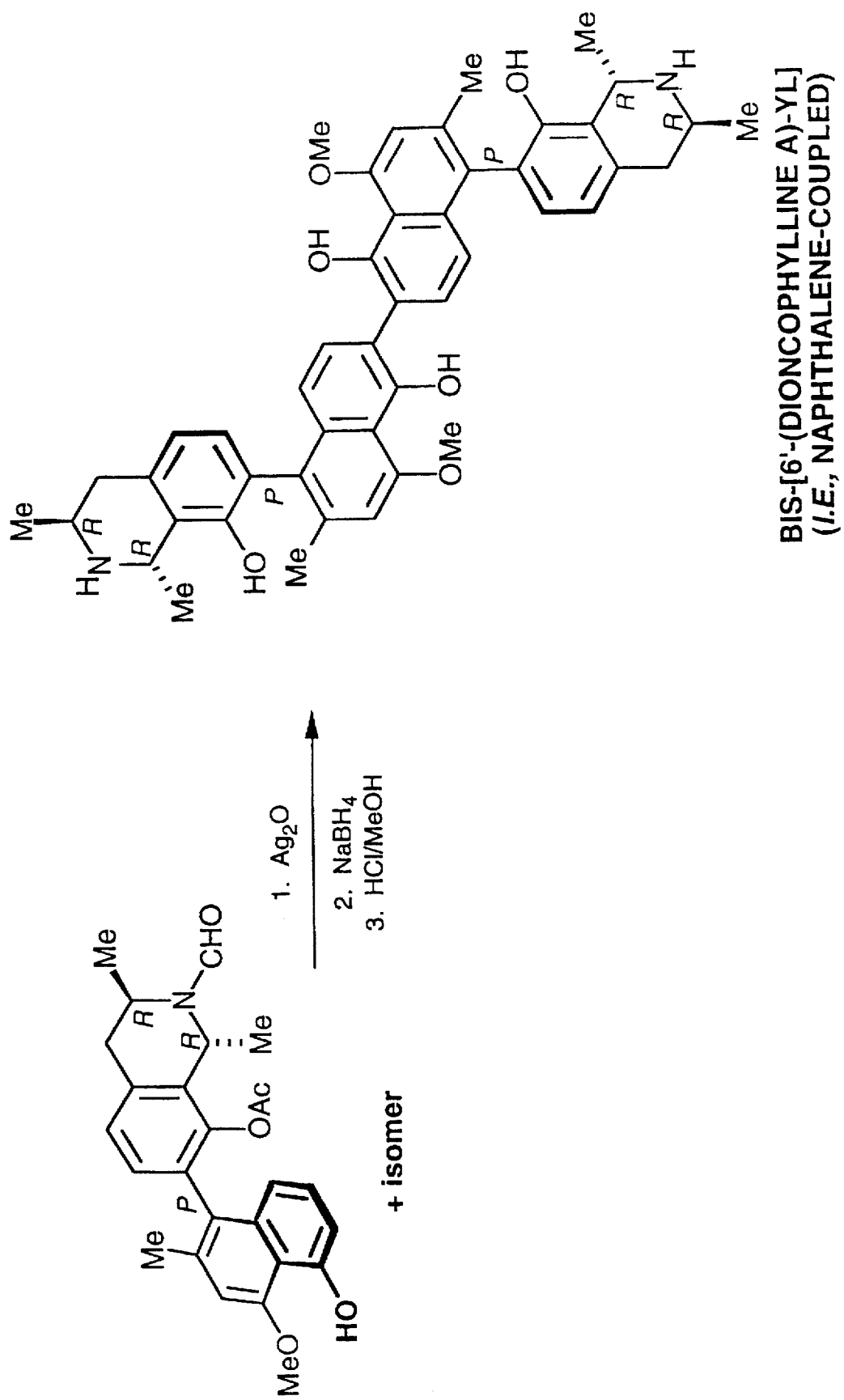
Figure 10:
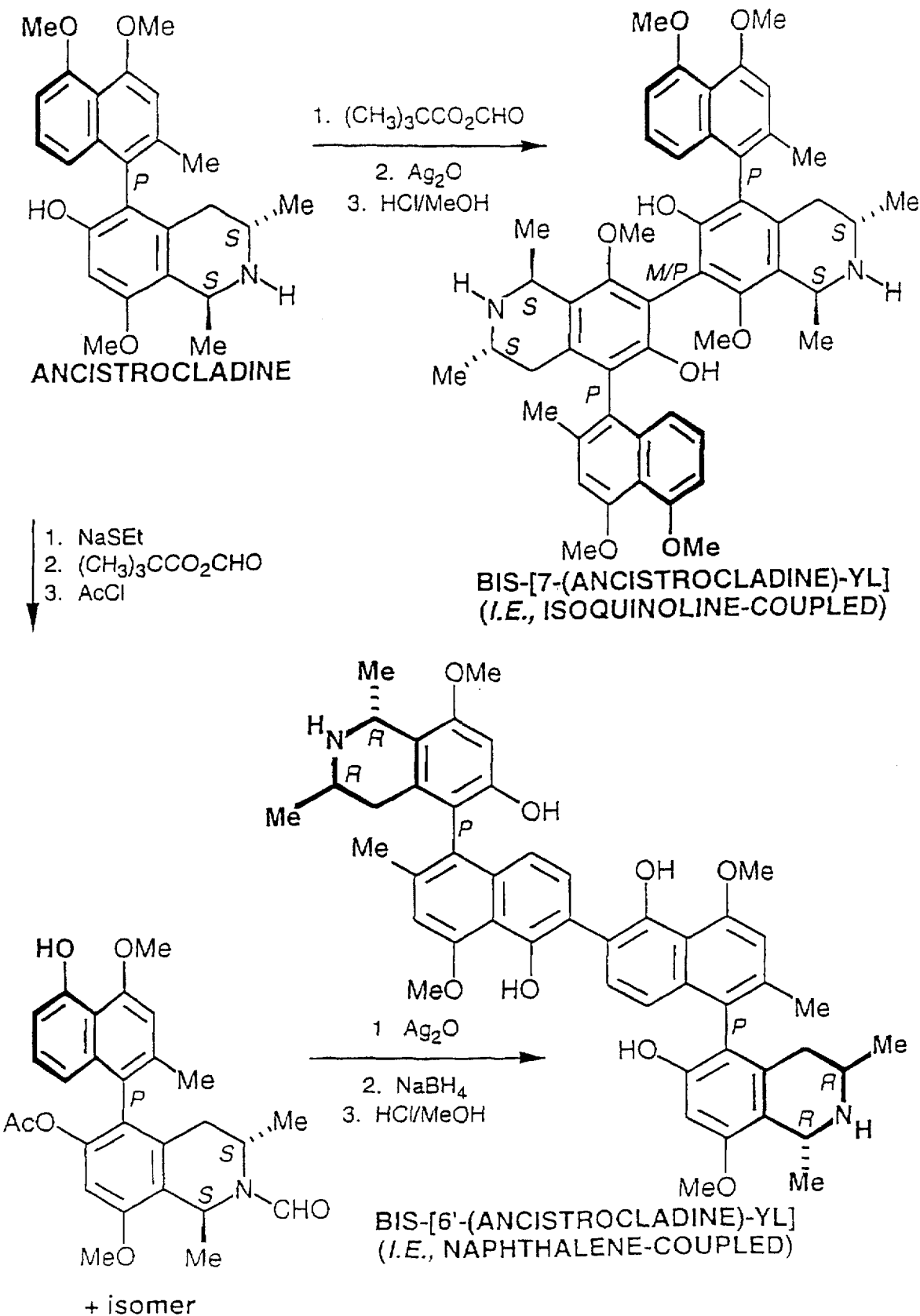
FIG. 10 illustrates a synthetic scheme for the preparation of isoquinoline-coupled versus naphthalene-coupled dimers of ancistrocladine.

In view of the present disclosures, one skilled in the art will appreciate that in certain instances with certain compounds there will be the opportunity of directly coupling, immediately following N-formylation, of selected naphthylisoquinoline monomers which do not have the free OH group on the naphthalene portion. This may be, for example, exploited to obtain dimers that are coupled at the isocyclic ring of the isoquinoline, giving rise to a quateraryl in which the naphthalene (N) and isoquinoline (IQ) parts are linked together with the connectivity "N-IQ-IQ-N", i.e., in a manner different than the usual (e.g., michellamine-type) naphthalene-coupled array ("IQ-N-N-IQ"). This is further exemplified in FIGS. 9 and 10, which schematically illustrate methods leading to isoquinoline-coupled or, optionally, to naphthalene-coupled dimers of dioncophylline A and ancistrocladine, respectively.

Accordingly, the present invention provides new dimeric naphthylisoquinoline alkaloids and derivatives thereof. In particular, the present invention provides a dimeric naphthylisoquinoline alkaloid comprised of coupled first and second naphthylisoquinoline monomers which are the same or different and wherein one or both of the monomers lacks a C-8' to C-5 naphthalene/isoquinoline linkage, particularly wherein the monomers which lack a C-8' to C-5 naphthalene/isoquinoline linkage are selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O,O-dimethyldioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$-$C_6$ alkyl, or cyano substituent, $CH_3$ may instead be H, and the tetrahydroisoquinoline may instead be a dihydroisoquinoline or a fully aromatic isoquinoline, while the monomer, if utilized, which possesses a C-8' to C-5 naphthalene/isoquinoline linkage is a compound of the formula

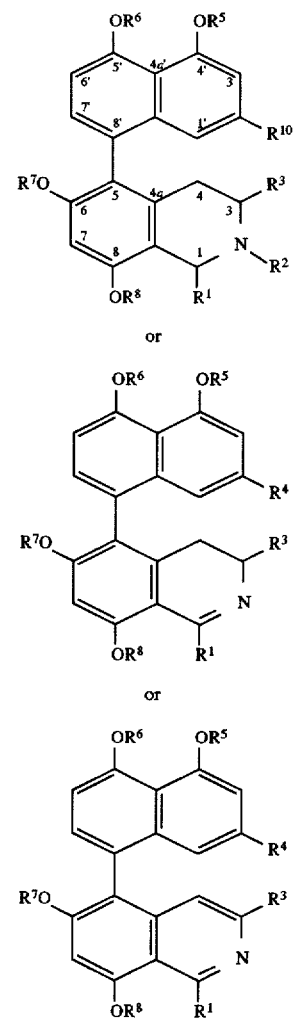

wherein $R^1$, $R^3$, $R^4$ and $R^{10}$ may be the same or different and each may be H or $C_1$-$C_6$ alkyl, $R^2$, $R^5$, $R^6$, $R^7$, and $R^8$ may be the same or different and each may be H, $C_1$-$C_6$ alkyl, $R^9CH_2$—, $R^9CO$—, or $R^9SO_2$—, $R^9$ may be H, $C_1$-$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$-$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

The following examples further illustrate the present invention, but, of course, should not be construed as in any way limiting its scope.

EXAMPLE 1: SYNTHESIS OF MICHELLAMINES

This example describes more fully the synthesis of a michellamine, specifically michellamine A (4). The method is summarized in FIG. 5; the reaction conditions and yields are summarized in the corresponding legend.

2: A mixture of korupensamine A (1) (50.0 mg, 0.13 mmol), pivalic formic anhydride (26 µl, 0.16 mmol) and dry $CH_2Cl_2$ (10 ml) was stirred at 20° C. for 2 h. Removal of the solvent in vacuum afforded a brown solid, which was dissolved in dry $CH_2Cl_2$ (10 ml). After addition of acetyl chloride (24 µl, 0.33 mmol), $NEt_3$ (46 µl, 0.33 mmol) and a catalytic amount of DMAP, the reaction mixture was stirred for 5 h. After treatment with aqueous $NH_4Cl$ (2M, 5 ml), the organic layer was filtered through deactivated (5% $NH_3$) silica gel. Crystallization from $CH_2Cl_2$/diethyl ether/ petroleum ether afforded 2 (58.4 mg, 0.12 mmol, 90%; m.p. 159° C., $[\alpha]_D^{20}$=+9.3 (c=0.50 in $CHCl_3$).

3: A solution of 2 (40.1 mg, 0.82 mmol) in dry $CHCl_3$ (50 ml) containing 0.2% $NEt_3$ was treated with $Ag_2O$ (401 mg, 1.73 mmol). After 5d stirring at 20° C., the solvent was removed and the residue purified by chromatography on deactivated (5% $NH_3$) silica gel with $CH_2Cl_2$/methanol (95:5) as eluent. The crude product was crystallized from $CH_2Cl_2$/diethylether/petroleum ether, to give 3 (33.9 mg, 5.20 µmol, 85%) as a deep-violet colored powder (m.p. decomp. >230° C., $[\alpha]_D^{20}$=+31 (c=0.0023 in $CHCl_3$)). The E-configuration at the central double bond was not established, but is plausible for steric reasons and in analogy to Laatsch (supra).

4: A solution of 3 (5.10 mg, 5.20 µmol) was treated with $NaBH_4$ (1.00 mg, 26.4 µmol) in dry iPrOH (1 ml) for 10 min at 20° C. The solvent was evaporated and the residue was dissolved in diethyl ether and extracted several times with water. The organic phases were dried over $Na_2SO_4$ and the solvent was evaporated under vacuum. A solution of the resulting oil in dry methanol (2 ml) was treated with portions (1 ml) of cold-saturated methanolic HCl over a period of 24 h while gently refluxing. After removal of the solvent, HPLC on a semi-preparative amino-bonded phase column (Rainin Dynamax-60A) with $CH_2Cl_2$/methanol/$(NH_4)_2CO_3$ (90:10:0.01) as eluent afforded 4 (2.64 mg, 3.48 µmol, 67%), which was characterized as its diacetate salt as described previously (Manfredi et al., supra; Boyd, et al., supra).

EXAMPLE 2: SYNTHESIS OF OTHER DIMERIC NAPHTHYLISOAUINOLINE ALKALOIDS

This example sets forth in further detail the synthesis of a representative new dimeric naphthylisoquinoline alkaloid, specifically, in this instance, a homodimer comprised of two monomeric dioncopeltine A "halves", which lack a C-8' to C-5 naphthalene/tetrahydroisoquinoline linkage. The method is outlined in FIG. 7; the reaction conditions and yields are summarized in the corresponding legend. Analogous to the above-mentioned procedure for korupensamine A dioncopeltine A (5) was submitted to the partial protection and dimerization sequence:

6: A suspension of 5 (190 mg, 0.50 mmol), $K_2CO_3$ (2070 mg, 1.50 mmol) and benzyl bromide (0.25 ml, 359 mg, 2.09 mmol) in acetone was refluxed for 4 h. Excessive $K_2CO_3$ was filtered off and the solvent was removed under vacuum. The crude product was crystallized from dichloromethane/ petroleum ether to afford the corresponding O,N-dibenzyldioncopeltine A (269 mg, 0.48 mmol) as colorless crystals (m.p. 150–151° C. $[\alpha]_D^{20}$=61.8° (c=0.5 in chloroform).

To a solution of this dibenzyldioncopeltine A (257 mg, 0.46 mmol) in dichloromethane (55 ml), $NEt_3$ (100 µl, 0.54 mmol) and a catalytic amount of DMAP were added. After stirring for 5 min at 20° C., acetyl chloride (55 µl, 0.77 mmol) was added. After stirring for 2h, the reaction mixture was quenched with saturated $NH_4Cl$-solution and the layers were separated. The solvent was evaporated and the residue was filtered over deactivated (7.5% $NH_3$) silica gel to afford 6 (273 mg, 0.45 mmol, 99%) as a light yellow oil.

7: A solution of 6 (20 mg, 0.33 mmol) in dry chloroform (2 ml) containing 0.2% triethylamine was treated with $Ag_2O$ (86 mg, 0.37 mmol). After 6h stirring at 20° C., the catalyst was filtered over deactivated (5% $NH_3$) silica gel to afford 7 as a deep violet amorphous powder.

8: A solution of 7 in methanol was irradiated ($\lambda$max =400 nm) at 20° C. for 2h. A catalytic amount of Pd-C (10%) was added and the suspension was hydrogenated at ambient $H_2$-pressure. The catalyst was filtered off (Celite) with methanol as eluent. The product was purified by HPLC.

EXAMPLE 3: SYNTHESIS OF DERIVATIVES OF DIMERIC NAPHTHYLISOQUINOLINE ALKALOIDS

This example more fully illustrates methods for obtaining medically useful new derivatives of naphthylisoquinoline alkaloids prepared according to the aforementioned methods of the present invention.

Using standard organic chemical methodology, one or more structural modifications of the aforementioned dimeric naphthylisoquinoline alkaloids prepared according to the present invention can be made to provide derivatives with modified biological properties which may be advantageously useful for treatment of certain host mammal species and/or against certain pathogenic agents. Such properties may, for example, include one or more of the following: greater therapeutic potency, broader spectrum of therapeutic activity, enhanced oral bioavailability, less host toxicity, more advantageous pharmacokinetics and/or tissue distribution.

Such methods were previously set forth by Boyd et al. (U.S. patent application Ser. No. 08/049,824) for michellamines. However, since the novel compounds of the present invention were not known at that time, these methods were not applied to these compounds. Accordingly, this example illustrates the modification of dimeric naphthylisoquinoline alkaloids other than the michellamines, and the derivatives resulting therefrom. Furthermore, this example sets forth novel methods of modification not disclosed therein.

Depending on the stoichiometric amount of the particular reactant, the naphthylisoquinoline compound can be substituted at one, some, or all of the respective available positions. For example, when such a compound is reacted with a certain amount of $CH_3COCl$, acetate can be introduced at one, some, or all the available OH or NH positions.

Examples of these include, but are not limited to:

1. Conversion to ester, sulfonate ester, and ether substituents at one or more phenolic hydroxyl positions in the naphthylisoquinoline compound.

For example, for preparation of esters or sulfonate esters, the selected naphthylisoquinoline compound can be reacted with an acid halide (RCOX or RSO$_2$X, where X=Cl, Br, or I, and R is an C$_1$–C$_6$ aliphatic or aromatic radical) in anhydrous pyridine or triethylamine.

Alternatively, the selected compound may be reacted with an acid (RCO$_2$H or RSO$_3$H wherein R is an aliphatic or aromatic radical) and dicyclohexylcarbodiimide in triethylamine to prepare the ester or sulfonate ester.

For preparation of ethers, the selected naphthylisoquinoline compound is reacted with an organic halide (e.g., RX, or RCH$_2$–X, where X=Cl, Br, I, OTf, or OTs, and R is a C$_1$–C$_6$ aliphatic or aromatic radical) in anhydrous acetone with anhydrous potassium carbonate or with phase transfer catalysis.

For instance:

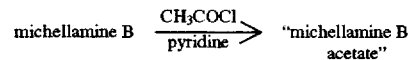
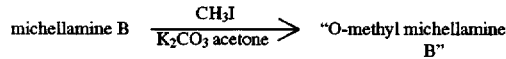

2. Removal of (an) ether methyl group(s) to provide a phenolic hydroxyl functionality and/or conversion of that moiety to an ester, sulfonate, or other ether.

For example, for hydrolytic cleavage of the methyl ether and conversion to phenolic hydroxyl, the selected naphthylisoquinoline compound is reacted with BBr$_3$, BX$_3$ (CH$_3$)$_2$S in CH$_2$Cl$_2$ (where X=F, Cl, or Br), FtS, or other ether cleaving reactants. The resulting phenol can be converted to esters, sulfonate esters or ethers as described above.

For instance:

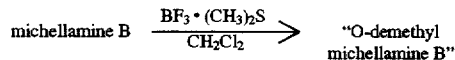

3. Preparation of amide or sulfonamide derivatives at the amine site in a selected naphthylisoquinoline compound.

For example, for preparation of amide or sulfonamide derivatives, the same general procedures described above (in 1) apply. In either case (1 or 3), an appropriate functional group protection strategy (blocking/deblocking of selected groups) is applied.

For instance:

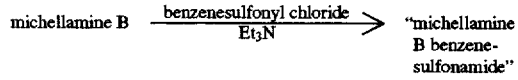

4. Conversion of the secondary amine functionality to an alkyl quaternary ammonium salt or to a tertiary amine.

For example, for preparation of tertiary amines, the selected naphthylisoquinoline alkaloid is reacted with an aldehyde and the resulting product reduced with NaBH$_4$.

Alternatively, for preparation of an alkyl ammonium salt, the selected naphthylisoquinoline alkaloid is reacted with an alkyl halide (RX, where X=Cl, Br, or I, and R is an C$_1$–C$_6$ aliphatic radical) in anhydrous aprotic solvent.

For instance:

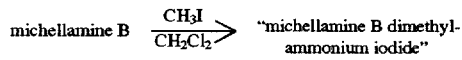

5. Substitution of one or more hydrogen substituents on the aryl systems by halogen, nitro, amino, hydroxyl, thiol, or cyano groups.

For example, for preparation of bromine-substituted derivatives, the selected naphthylisoquinoline compound is reacted with Br$_2$ in H$_2$O, HOAC, or CHCl$_3$. For preparation of other substituted derivatives, the selected naphthylisoquinoline compound is treated with HNO$_3$/HOAc to provide nitro-substituted (–NO$_2$) derivatives. In turn, the nitro derivative can be reduced to the amino derivative. The amino-derivative is the point of origin of the chloro, iodo, cyano, thiol, and hydroxyl substitution via well known and practiced diazonium substitution reactions.

For instance:

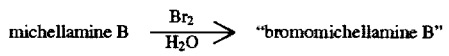
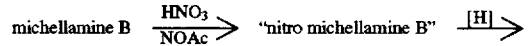
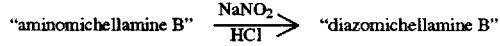
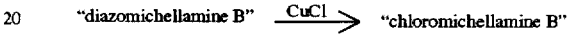
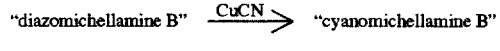
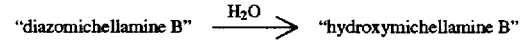

Additionally, the following new modifications are disclosed herein:

1. Conversion of the tertiary amine function (which may be prepared by reaction (4)) to a secondary amine.

For example, for preparation of a secondary amine, a selected N-alkyl naphthylisoquinoline compound is reacted with cyanogen bromide to give the corresponding cyanamide, which is then treated with LiAlH$_4$.

For instance:

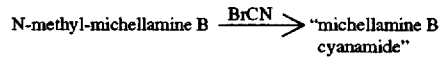
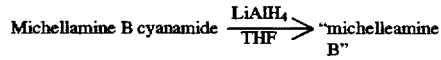

2. Conversion of one or more phenolic hydroxyl groups to an aromatic hydrogen substituent.

For example, the selected naphthylisoquinoline compound is converted (after suitable protection of the amine function if necessary) to the triflic ester, followed by reductive deoxygenation of the triflic ester to give the corresponding 6-deoxykorupensamine.

For instance:

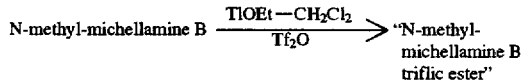
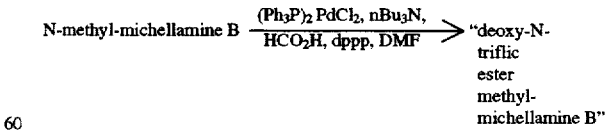

3. Substitution of one or more hydrogen substituents on the aryl systems by acyl or alkyl.

For example, for preparation of an acyl derivative, the suitably protected (e.g., N-benzylated) naphthylisoquinoline is reacted with RCOCl and AlCl$_3$ to give a corresponding acyl derivative, which can then be deprotected (e.g., by N-debenzylation) if desired. For preparation of the corresponding alkyl naphthylisoquinoline, the acyl naphthylisoquinoline is treated with $LiAlH_4/AlCl_3$.

4. Replacement of a methyl group with a hydrogen substituent.

For example, a methyl-substituted naphthylisoquinoline may be oxidized to give a corresponding carboxyl-substituted naphthylisoquinoline, which may then be decarboxylated to give the final desired (demethylated) naphthylisoquinoline.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A dimeric naphthylisoquinoline alkaloid comprised of coupled first and second naphthylisoquinoline alkaloid monomers which are the same or different, wherein said first

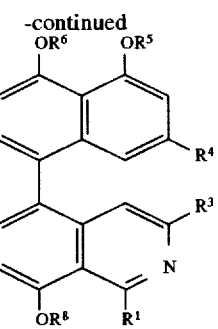

and second monomers are compounds of the formula

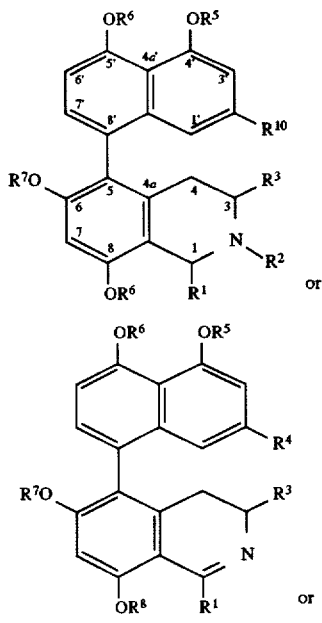

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine, with the proviso that $R^{10}$ is not methyl in both first and second monomers when $R^1$ and $R^3$ are methyl in both first and second monomers.

2. The dimeric naphthylisoquinoline alkaloid of claim 1, wherein said first and second monomers are the same.

3. The dimeric naphthylisoquinoline alkaloid of claim 1, wherein said first and second monomers are different.

4. A dimeric naphthylisoquinoline alkaloid comprised of coupled first and second naphthylisoquinoline alkaloid monomers which are the same or different, wherein said first monomer lacks a C-8' to C-5 naphthalene/isoquinoline linkage, and said second monomer may or may not possess a C-8' to C-5 naphthalene/isoquinoline linkage.

5. The dimeric naphthylisoquinoline alkaloid of claim 4, wherein said second monomer possesses a C-8' to C-5 naphthalene/isoquinoline linkage.

6. The dimeric naphthylisoquinoline alkaloid of claim 4, wherein said second monomer lacks a C-8' to C-5 naphthalene/isoquinoline linkage and said first and second monomers are the same.

7. The dimeric naphthylisoquinoline alkaloid of claim 4, wherein said second monomer lacks a C-8' to C-5 naphthalene/isoquinoline linkage and said first and second monomers are different.

8. The dimeric naphthylisoquinoline alkaloid of claim 4, wherein said first monomer is selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O- pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$–$C_6$ alkyl, or cyano substituent, $CH_3$ may instead be H, and the tetrahydroisoquinoline may instead be a dihydroisoquinoline or a fully aromatic isoquinoline.

9. The dimeric naphthylisoquinoline alkaloid of claim 8, wherein said second monomer is a compound of the formula

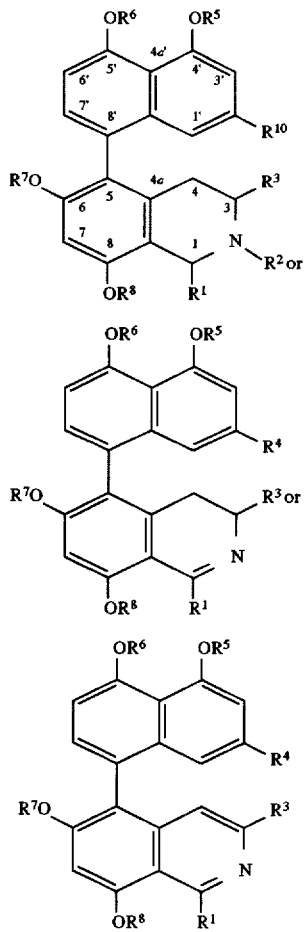

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

10. The dimeric naphthylisoquinoline alkaloid of claim 8, wherein said first and second monomers are the same.

11. The dimeric naphthylisoquinoline alkaloid of claim 8, wherein said first and second monomers are different, and second monomer is selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$–$C_6$ alkyl, or cyano substituent, $CH_3$ may instead be H, and the tetrahydroisoquinoline may instead be a dihydroisoquinoline or a fully aromatic isoquinoline.

12. A dimeric naphthylisoquinoline compound comprising coupled first and second naphthylisoquinoline monomers which are the same, wherein said first and second monomers are coupled through a carbon-carbon bond and wherein said first and second monomers lack a C-8' to C-5 naphthalene/isoquinoline linkage.

13. The compound of claim 12, wherein said first and second monomers are selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$–$C_6$ alkyl, or cyano substituent, $CH_3$ may instead be H, and the tetrahydroisoquinoline may instead be a dihydroisoquinoline or a fully aromatic isoquinoline.

14. The compound of claim 12, wherein said first and second monomers possess a C-8' to C-5 naphthalene/isoquinoline linkage, and are compounds of the formula

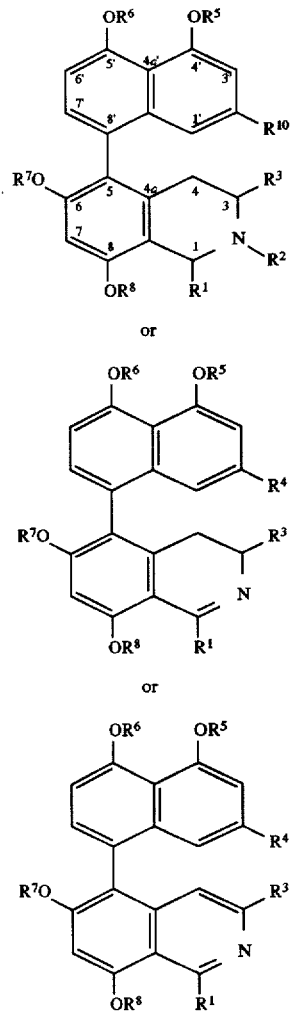

wherein $R^1$, $R^3$, $R^4$, and $R^{10}$ may be the same or different and each may be H or $C_1$–$C_6$ alkyl, $R^2$, $R^5$, $R_6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7, 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine, with the proviso that $R^{10}$ is not methyl in both first and second monomers when $R^1$ and $R^3$ are methyl in both first and second monomers.

15. A dimeric naphthylisoquinoline compound comprising coupled first and second naphthylisoquinoline monomers, wherein said first and second monomers are different.

16. The compound of claim 15, wherein said first and second monomers possess a C-8' to C-5 naphthalene/isoquinoline linkage.

17. The compound of claim 15, wherein said first and second monomers lack a C-8' to C-5 naphthalene/isoquinoline linkage.

18. The compound of claim 15, wherein said first monomer lacks a C-8' to C-5 naphthalene/isoquinoline linkage and said second monomer possesses a C-8' to C-5 naphthalene/isoquinoline linkage.

19. The compound of claim 15, wherein said first monomer is a compound of the formula

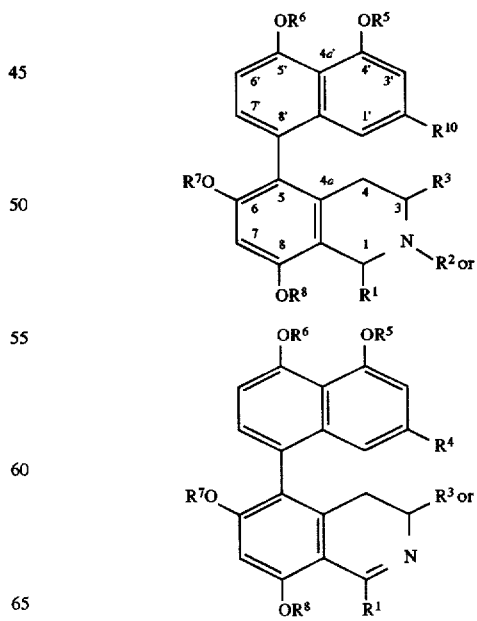

-continued

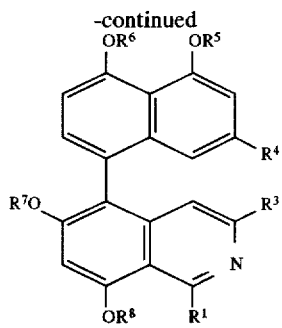

wherein $R^1$, $R^3$, $R^4$, and $R^{10}$ may be the same or different and each may be H or $C_1$–$C_6$ alkyl, $R^2$, $R^5$, $R_6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine, and said second monomer is selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, Nformyl-8-O-benzoyl-dioncophylline C, and 8-O-methyl-dioncophylline C, wherein the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$–$C_6$ alkyl, or cyano substituent, $CH_3$ may instead be H, and the tetrahydroisoquinoline may instead be a dihydroisoquinoline or a fully aromatic isoquinoline.

20. The compound of claim 15, wherein said first and second monomers are compounds of the formula

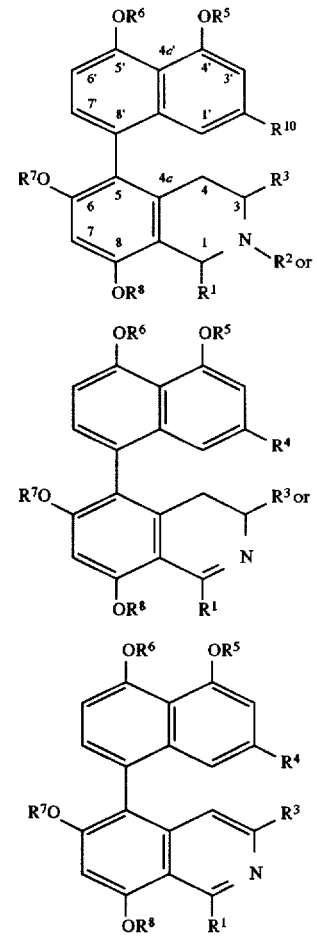

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

21. The compound of claim 15, wherein said first and second monomers are selected from the group consisting of dioncophylline B, dioncopeltine A, dioncophylline A, dioncophylline C, dioncolactone A, N-methyl-dioncophylline A, ancistrobrevine D, ancistrocladine, 5-O-demethyl-8-O-methyl-7-epi-dioncophylline A, 5'-O-demethyl-7-epi-dioncophylline A, dioncophylleine A, (±)-dioncophyllacine A. hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O, O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein the configurations at C-1 and C-3 may be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, one or more aromatic hydrogen substituent(s) may instead be a halogen, nitro, amino, hydroxyl, thiol, acyl, $C_1$–$C_6$ alkyl, or cyano substituent, $CH_3$ may instead be H, and the tetrahydroisoquinoline may instead be a dihydroisoquinoline or a fully aromatic isoquinoline.

22. A dimeric naphthylisoquinoline alkaloid comprised of coupled first and second naphthylisoquinoline alkaloid monomers of the formula

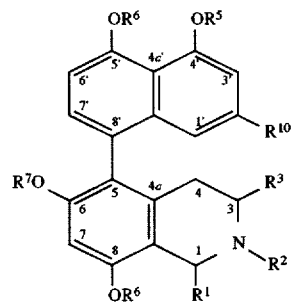

wherein $R^1$, $R^3$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, with the proviso that said dimeric naphthylisoquinoline is not a michellamine.

23. The dimeric naphthylisoquinoline alkaloid of claim 22, wherein at least one of $R^1$, $R^3$, $R^5$, and $R^{10}$ on said first or second naphthylisoquinoline monomer is H.

24. The dimeric naphthylisoquinoline alkaloid of claim 22, wherein at least two of $R^1$, $R^3$, $R^5$, and $R^{10}$ on said first or second naphthylisoquinoline monomer are H.

* * * * *